United States Patent
Bonde et al.

(10) Patent No.: US 9,950,179 B2
(45) Date of Patent: Apr. 24, 2018

(54) MEDICAL DEVICES FOR TRIAL STIMULATION

(71) Applicant: Medtronic, Inc., Minneapolis, MN (US)

(72) Inventors: Eric H. Bonde, Minnetonka, MN (US); Xuan K. Wei, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1007 days.

(21) Appl. No.: 13/658,278

(22) Filed: Oct. 23, 2012

(65) Prior Publication Data
US 2013/0110201 A1    May 2, 2013

Related U.S. Application Data

(60) Provisional application No. 61/552,836, filed on Oct. 28, 2011.

(51) Int. Cl.
| A61N 1/36 | (2006.01) |
| A61N 1/375 | (2006.01) |
| A61N 1/378 | (2006.01) |
| A61N 1/372 | (2006.01) |

(52) U.S. Cl.
CPC ......... A61N 1/375 (2013.01); A61N 1/36125 (2013.01); A61N 1/3787 (2013.01); A61N 1/37229 (2013.01); A61N 1/37241 (2013.01); A61N 1/3752 (2013.01)

(58) Field of Classification Search
CPC ...................................... A61N 1/375
USPC ............................................. 607/59, 60, 61
See application file for complete search history.

(56) References Cited

U.S. PATENT DOCUMENTS

| 5,630,836 A * | 5/1997 | Prem et al. ..................... 607/61 |
| 5,662,694 A * | 9/1997 | Lidman .................... A61N 1/37 607/60 |
| 7,065,412 B2 * | 6/2006 | Swoyer .................. A61N 1/378 607/116 |
| 7,640,059 B2 | 12/2009 | Forsberg et al. |
| 7,680,540 B2 | 3/2010 | Jensen et al. |
| 2004/0172090 A1 * | 9/2004 | Janzig ................. A61N 1/3605 607/45 |
| 2007/0260295 A1 * | 11/2007 | Chen .................... A61N 5/0601 607/88 |

* cited by examiner

*Primary Examiner* — Alyssa M Alter
(74) *Attorney, Agent, or Firm* — Shumaker & Sieffert, P.A.

(57) ABSTRACT

Devices, systems, and techniques for delivering trial stimulation therapy to a patient are disclosed. A trial neurostimulator (e.g., an IMD) may be implanted within a patient to deliver stimulation therapy during a relatively short trial period of time. This IMD may include limited circuitry and be powered by an external power source to minimize the size of the IMD within the patient. The IMD may include a non-hermetic housing capable of protecting the IMD circuitry for the trial period of time. In one example, the IMD may include a secondary coil configured to generate an electrical signal in response to a magnetic field generated by an external primary coil, circuitry configured to generate a stimulation signal in response to the electrical signal, and a non-hermetic implantable housing configured to encase or otherwise house the secondary coil and the circuitry.

30 Claims, 11 Drawing Sheets

MEDICAL DEVICES FOR TRIAL STIMULATION

CROSS-REFERENCE TO RELATED APPLICATIONS

The present application claims priority to U.S. Provisional Patent Application No. 61/552,836, filed Oct. 28, 2011, which application is hereby incorporated by reference as if re-written in its entirety.

TECHNICAL FIELD

The disclosure relates to implantable medical devices and, more particularly, medical devices that deliver trial stimulation therapy.

BACKGROUND

Electrical stimulation is an effective therapy for a variety of conditions and diseases that adversely affect patient health. For example, electrical stimulation has been effective in alleviating chronic pain, movement disorders, gastrointestinal disorders, and pelvic floor disorders. Spinal cord stimulation systems have been found to provide relief for chronic pain. Deep brain stimulation can be effective in treatment of movement disorders such as Parkinson's disease, as well as other neurological disorders such as epilepsy. Stimulation of the gastrointestinal tract can be effective in alleviating gastroparesis and obesity. Stimulation of the pelvic floor can be effective in alleviating urinary incontinence, fecal incontinence, pelvic pain, and sexual dysfunction.

Typically, electrical stimulation is delivered by an implantable pulse generator that is chronically implanted within the patient. One or more leads extending from the implantable pulse generator carry electrodes for delivery of stimulation energy to a target tissue or nerve site. A physician may prescribe a course of trial or "screening" stimulation to evaluate the likely efficacy of electrical stimulation therapy for the patient. This trial may include a trial lead percutaneously implanted within the patient and coupled to an external trial stimulator. The trial stimulator may be used to evaluate the efficacy of stimulation before implanting a chronic lead and a chronic stimulator. A chronic stimulator typically requires surgical implantation and may be implanted for several years. Upon successful trial stimulation, a chronic lead and chronic stimulator may be implanted within the patient.

SUMMARY

In general, the disclosure is directed to devices, systems, and techniques for delivering trial stimulation therapy to a patient. A trial neurostimulator may be implanted within a patient to deliver stimulation therapy during a relatively short trial period of time. This trial neurostimulator may include limited circuitry and be powered by an external power source to minimize the size of the trial neurostimulator. The trial neurostimulator may include a non-hermetic housing capable of protecting the circuitry for a trial period of time. A trial period of time may be substantially less than a chronic period of time. In one example, the trial neurostimulator may include a permanently coupled medical lead. In another example, the trial neurostimulator may be configured to couple with a chronic medical lead such that the trial neurostimulator may be replaced with a chronic neurostimulator after successful trial therapy. In this case, the chronic lead may be used for both trial stimulation and chronic stimulation and need not be explanted following trial stimulation.

In one aspect, the disclosure is directed to an implantable medical device that includes a secondary coil configured to generate an electrical signal in response to a magnetic field generated by an external primary coil, circuitry configured to generate a stimulation signal in response to the electrical signal, and a non-hermetic implantable housing configured to house the secondary coil and the circuitry.

In another aspect, the disclosure is directed to a system that includes means for generating an electrical signal in response to a magnetic field, means for generating a stimulation signal in response to the electrical signal, means for delivering the stimulation signal to a patient, and means for non-hermetically housing the means for generating the electrical signal and means for generating the stimulation signal.

In a further aspect, the disclosure is directed to a method that includes generating an electrical signal by a secondary coil in response to a magnetic field, and generating a stimulation signal by circuitry in response to the electrical signal, wherein the secondary coil and the circuitry are housed by a non-hermetic housing implanted within a patient.

In a further aspect, the disclosure is directed to a system that includes an implantable medical device and an introducer. The implantable medical device includes a secondary coil configured to generate an electrical signal in response to a magnetic field generated by an external primary coil, circuitry configured to generate a stimulation signal in response to the electrical signal, a non-hermetic housing configured to house the secondary coil and the circuitry, and a medical lead permanently coupled to the circuitry and at least partially covered by the non-hermetic housing, wherein the medical lead is configured to deliver the stimulation signal to the patient. The introducer includes a sheath configured to accept at least a portion of the medical lead, wherein the sheath comprises at least one structural characteristic configured to facilitate splitting the sheath along a length of the sheath and a handle configured to separate the sheath along the at least one structural characteristic in response to a force directed away from the implantable medical device.

The details of one or more example are set forth in the accompanying drawings and the description below. Other features, objects, and advantages will be apparent from the description and drawings, and from the claims.

DETAILED DESCRIPTION

Figure 1:
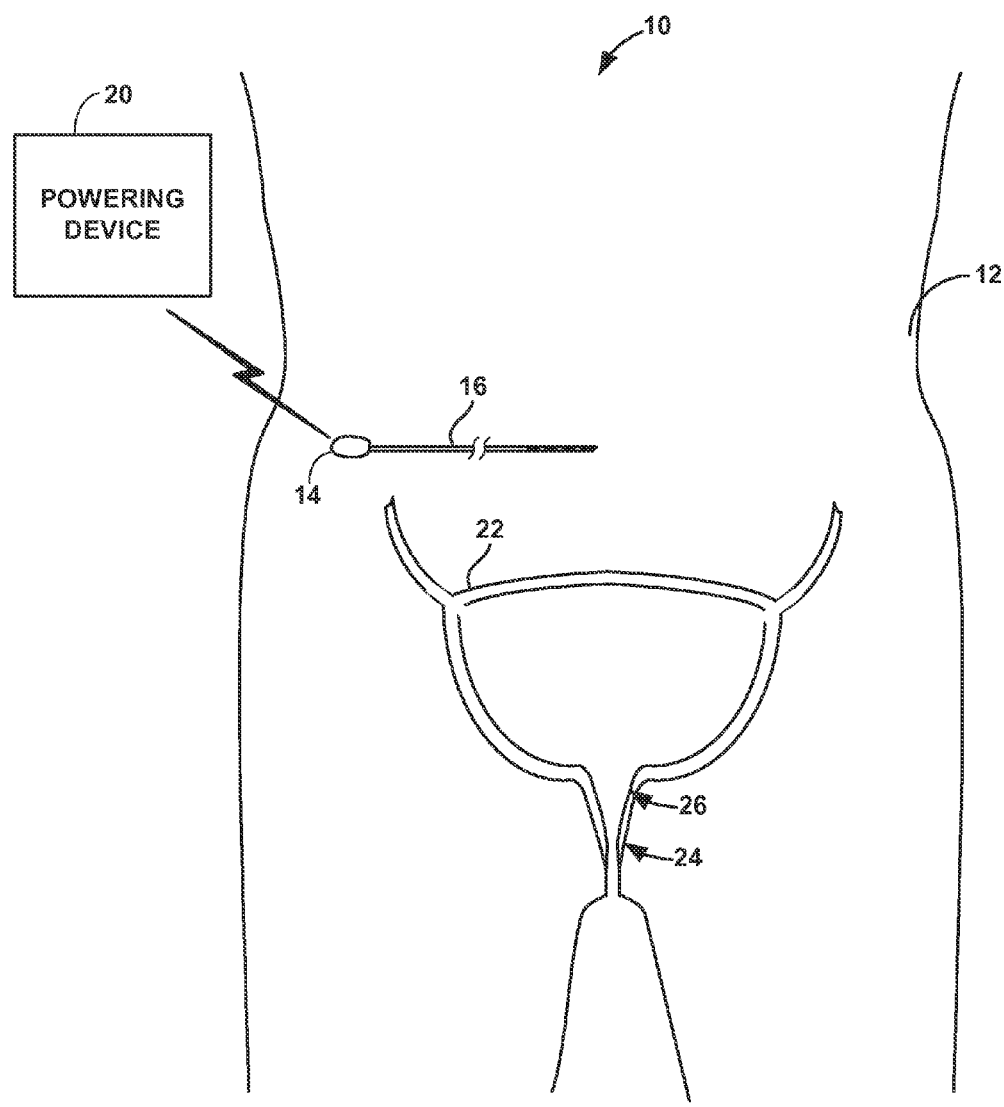
FIG. 1 is a conceptual diagram illustrating an example system that includes an implantable trial neurostimulator and an external powering device that provides operational power to the trial neurostimulator.

This disclosure is directed to devices, systems, and techniques for delivering trial stimulation therapy to a patient. Electrical stimulation therapy may be delivered to a patient for a variety of different therapeutic purposes. For example, electrical stimulation therapy may be provided to alleviate chronic pain, movement disorders, gastrointestinal disorders, and pelvic floor disorders (e.g., urinary and fecal incontinence). Prior to implanting a chronic stimulation system for treatment, trial stimulation therapy may be provided to the patient to evaluate the patient's response to the therapy. Trial stimulation therapy may include the implantation of a temporary lead (e.g., a trial lead) that is implanted within the patient. The trial lead, or a lead extension, may exit the skin (e.g., a percutaneous lead) during the trial period. The trial lead is then coupled to an external trial stimulator that generates the stimulation signal delivered to the patient via the trial lead.

This trial period may allow the patient to evaluate the intended therapy without extensive surgery, patient time, clinician time, and patient discomfort. In addition, the trial period may be completed at a reduced cost of the trial system instead of requiring the full cost of a chronic therapy system. However, typical trial stimulation systems also require a temporary lead to exit the skin that increases the patient's exposure to bacteria and other pathogens that may result in complications for the patient. To minimize infection during the trial period, the patient may also need to refrain from certain activities that may introduce a pathogen (e.g., bathing). In some examples, a successful trial period may not result in equally effective chronic stimulation if electrodes of a chronic lead are not positioned in the exact anatomical location as the electrodes of a removed trial lead. In other words, the chronic stimulation therapy may not be perceived (e.g., felt) in the same way that the trial stimulation therapy was perceived.

As disclosed herein, a trial stimulation system may be provided that enables trial stimulation therapy without the need for a percutaneous lead. Although the trial period may only last for several days or weeks, a fully closed skin surface may reduce the risk of infection during the trial period. According to some examples of this disclosure, the trial neurostimulator, e.g., a trial implantable medical device (trial IMD), may be inexpensively manufactured such that it may be disposable after the trial period is complete. In one example, the trial IMD may include a secondary coil for receiving operational power from an external primary coil (e.g., via inductive coupling) and a therapy module that generates a stimulation signal delivered to the patient via a coupled lead. In other example, the trial IMD may only receive the secondary coil and a filter module such that the stimulation signal is received directly from the external primary coil via inductive coupling and delivered to the patient. Although a trial IMD may require an external powering device to operate (e.g., the trial IMD does not include a power source), the powering device may be reusable between patients. Also, trial IMDs with minimal circuitry may reduce the cost of each trial IMD.

The cost of the trial IMD may also be reduced without a hermetic housing. Since the trial IMD may only be implanted for a relatively short period of time (e.g., a period of hours, days, or weeks), the housing that contains the trial IMD circuitry may not need to be "hermetic." Typically, biocompatible metal alloys (e.g., titanium alloys) are used to protect circuitry of implantable devices from caustic body fluids. However, these metal alloys are relatively expensive. Therefore, a more permeable material such as epoxy may be used to construct a non-hermetic housing for the trial IMD that sufficiently protects the circuitry from body fluids and the patient from circuitry for the duration of the trial period.

In some examples, the trial IMD may include a permanently coupled lead that is removed from the patient after the trial period. In other examples, the trial IMD may be removably coupled to a chronic lead configured to remain with the patient during both the trial and the chronic therapy periods. The trial IMD may include a header or set of contacts that accepts the connectors of the chronic lead. Alternatively, the trial IMD may include a lead extension permanently coupled within the housing. A distal end of the lead extension may include a set of contacts to which contacts of the chronic lead may be electrically coupled. In these examples, the chronic lead may increase the likelihood that successful trial therapy continues as successful chronic therapy due to not displacing implanted electrodes with respect to target tissue within the patient.

Although trial IMDs are described herein as being used to evaluate potential chronic stimulation therapy, these trial IMDs may also be used to deliver a short term therapy without an intended chronic therapy counterpart. In other words, a patient may only need to receive stimulation therapy over a relatively short time period (e.g., a several days, weeks, or months). This therapy may be useful, for example, to treat pain during recovery from a traumatic injury or provide functional treatment while the patient waits to receive more permanent surgery to remedy the condition. In this manner, a trial IMD with a non-hermetic housing may be a cost-effective and minimally invasive solution to treat certain patient conditions.

FIG. 1 is a conceptual diagram illustrating an example system 10 that includes an implantable trial neurostimulator (trial IMD) 14 and an external powering device 20 that provides operational power to trial IMD 14. Although the techniques described in this disclosure are generally applicable to a variety of medical devices including medical devices such as patient monitors, electrical stimulators, or drug delivery devices, application of such techniques to implantable neurostimulators will be described for purposes of illustration. More particularly, the disclosure will refer to an implantable neurostimulation system for use in incontinence stimulation therapy, but without limitation as to other types of medical devices. For example, trial IMD 14 may instead be applicable to spinal cord stimulation therapy.

As shown in FIG. 1, system 10 includes trial IMD 14 and external charging device 20 shown in conjunction with a patient 12, who is ordinarily a human patient. In the example of FIG. 1, trial IMD 14 is an implantable electrical stimulator that delivers neurostimulation therapy to patient 12, e.g., for relief of urinary incontinence, pelvic floor pain or other symptoms. Generally trial IMD 14 may be a trial electrical stimulator intended to be implanted within patient 12 for days, weeks, or months. For example, trial IMD 14 may only be implanted for a trial period of four weeks or less. In this manner, trial IMD 14 may be used to screen or evaluate the efficacy of electrical stimulation for chronic therapy without the need of a chronic neurostimulator. In the example of FIG. 1, trial IMD 14 and lead 16 may deliver electrical stimulation directed to alleviate bladder dysfunction, such as an overactive bladder, urgency, urinary retention, or urinary incontinence. Trial IMD 14 may be implanted in a subcutaneous tissue pocket, within one or more layers of muscle, or other internal location. Although trial IMD 14 may be constructed of dimensions small enough to implant trial IMD 14 in any physiological location that accommodates lead 16, trial IMD 14 may be implanted at a subcutaneous location that may accommodate a chronic neurostimulator if the trial stimulation is successful. Lead 16 may be permanently or removably coupled to trial IMD 14.

Electrical stimulation energy, which may be constant current or constant voltage based pulses, for example, is delivered from trial IMD 14 to one or more targeted locations within patient 12 via one or more electrodes (not shown) of lead 16. The electrodes carried by lead 16 may be located at a distal end of lead 16 and/or at any location long the length of lead 16. The parameters for a program that controls delivery of stimulation energy by trial IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example. Trial IMD 14 may include a stimulation generator (e.g., a therapy module) configured to generate stimulation signals substantially similar to that of a chronic neurostimulator. However, the therapy module of trial IMD 14 may provide fewer options, store fewer therapy programs, or otherwise provide fewer features common to a chronic neurostimulator. In this manner, trial IMD 14 may only include circuitry necessary for patient 12 to evaluate the efficacy of neurostimulation therapy.

In the example of FIG. 1, lead 16 is disposed within patient 12, e.g., implanted within patient 12. Lead 16 tunnels through tissue of patient 12 from the implant site of trial IMD 14 to a nerve associated with pelvic floor tissue (e.g., a sacral nerve). Although lead 16 may be a single lead, lead 16 may include a lead extension or other segments that may aid in implantation or positioning of lead 16. In addition, a proximal end of lead 16 may include a connector (not shown) that electrically couples to a connector of trial IMD 14. Although only one lead 16 is shown in FIG. 1, system 10 may include two or more leads, each coupled to trial IMD 14 and directed to similar or different target tissue sites. For example, multiple leads may be disposed within the pelvic floor and/or other locations within patient 12.

Lead 16 may carry one or more electrodes that are placed adjacent to the target tissue, e.g., a sacral nerve for sacral nerve stimulation therapy. One or more electrodes may be disposed at a distal tip of lead 16 and/or at other positions at intermediate points along lead 16, for example. Electrodes of lead 16 transfer electrical stimulation generated by an electrical stimulation generator, e.g., a therapy module, in trial IMD 14 to tissue of patient 12. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 16 and will be described for purposes of illustration.

In alternative examples, lead 16 may be configured to deliver stimulation energy generated by trial IMD 14 to stimulate one or more spinal nerves or the spinal cord of patient 12. Lead 16 and trial IMD 14 may also be configured to provide other types of electrical stimulation or drug therapy (e.g., with lead 16 configured as a catheter) in other examples. For example, trial IMD 14 and lead 16 may be configured to provide deep brain stimulation (DBS), peripheral nerve stimulation (PNS), or other deep tissue or superficial types of electrical stimulation. In other examples, lead 16 may provide one or more sensors configured to allow trial IMD 14 to monitor one or more parameters of patient 12. The one or more sensors may be provided in addition to, or in place of, therapy delivery by lead 16.

Trial IMD 14 delivers electrical stimulation therapy to patient 12 via selected combinations of electrodes carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 may be tissue proximate a sacral nerve that innervates a urinary sphincter or other pelvic floor muscle.

Although lead 16 is described as generally delivering or transmitting electrical stimulation signals, lead 16 may additionally or alternatively transmit electrical signals from patient 12 to trial IMD 14 for monitoring. For example, IMD 14 may utilize detected nerve impulses to diagnose the condition of patient 12 or adjust the delivered stimulation therapy. Lead 16 may thus transmit electrical signals to and from patient 12.

A user, such as a clinician or patient 12, may interact with a user interface of an external programmer (not shown) to program trial IMD 14. Programming of IMD 14 may refer generally to the generation and transfer of commands, programs, or other information to control the operation of trial IMD 14. For example, the external programmer may transmit programs, parameter adjustments, program selections, group selections, or other information to control the operation of IMD 14, e.g., by wireless telemetry or wired connection. This wireless telemetry may be performed using the same coil of IMD 14 that receives operational power or a different structure (e.g., an antenna) to receive communication signals using wireless telemetry.

In some cases, an external programmer may be characterized as a physician or clinician programmer if it is primarily intended for use by a physician or clinician. In other cases, the external programmer may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use. In other examples, external charging device 20 may be part of an external programmer, perform the functions of an external programmer, or communicate with an external programmer. In this manner, a user may program and charge trial IMD 14 using one device, or multiple devices. In addition, these multiple devices may need to communicate with each other in order to charge and/or program trial IMD 14.

Powering device 20 may be used to provide operational power to trial IMD 14 within patient 12. Trial IMD 14 may not include a battery or a rechargeable battery that provides operational power. Instead, operation of trial IMD 14 may require power being transmitted from powering device 20 for electrical stimulation to be delivered to patient 12 via lead 16. Trial IMD 14 may include circuitry to condition the power received from powering device 20. For example, trial IMD 14 may include rectification, filtering, and voltage and/or current regulation circuitry to produce operating power for stimulation generation circuitry, processing/control circuitry, telemetry circuitry, sensing circuitry, and/or other circuitry associated with trial IMD 14. In general, trial IMD 14 may be unable to deliver stimulation therapy without concurrently receiving power from powering device 20. Powering device 20 may transmit operational power to trial IMD 14 via inductive coupling. Powering device 20 may include a primary coil that produces a magnetic field with electrical current generated within the primary coil. When the primary coil is aligned with a secondary coil of trial IMD 14, the magnetic field may induce an electrical current used to power a therapy module within IMD 14. In other examples, powering device 20 may transmit stimulation signals directly to IMD 14 for delivery to patient 12. For example, signals transmitted by powering device 20 may be transmitted with desired characteristics, such as amplitude, pulse rate, and/or pulse width, received by trial IMD 14 by inductive coupling, and then applied directly or indirectly to stimulation electrodes, i.e., as stimulation pulses or waveforms, by circuitry within trial IMD 14. In either case, trial IMD 14 may require power from powering device 20 at any time trial stimulation therapy is to be delivered to patient 12.

Powering device 20 may be positioned in close proximity to trial IMD 14 such that the primary and secondary coils can be aligned. Patient 12 may need to hold powering device 20 against the skin, or alternatively, powering device 20 may be attached to patient 12 using a belt, sutures, or adhesives. Powering device 20 may include the primary coil within a housing of the powering device. Alternatively, powering device 20 may be tethered to the primary coil such that the primary coil is more easily positioned on patient 12. In some examples, powering device 20 may include a power source and primary coil to transfer power to IMD 14. In other examples, powering device 20 may also include a user interface that allows a user to program one or more parameters that define the power transmitted from powering device 20. This user interface may also be used to set stimulation parameters if the power transmitted to trial IMD 14 includes the stimulation signal for therapy. Although inductive coupling is described herein for transmitting power between powering device 20 and trial IMD 14, other wireless transmission techniques may be used in other examples.

Powering device 20 may thus be a means for generating a magnetic field external to patient 12. The electrical parameters used to define the magnetic field from the primary coil of powering device 20 may be selected to transmit operating power to a therapy module within trial IMD 14. In another example, the electrical parameters used to define the magnetic field may be selected to induce the electrical signal in the secondary coil containing the simulation signal. The electrical parameters of the primary coil in powering device 20 may thus be directed to result in a stimulation signal usable to provide trial stimulation therapy to patient 12.

As described herein, trial IMD 14 may be a neurostimulator configured for providing electrical stimulation to patient 12 for a relatively short period of time e.g., a few weeks or months. This short period of time may be a trial period in which electrical stimulation therapy is evaluated by patient 12. Trial IMD 14 may be constructed to minimize size and minimize cost while only needing to remain operational for the relatively short trial period. After the trial period, trial IMD 14 may be removed from patient 12. If the trial therapy was successful at treating patient 12, a chronic neurostimulator containing a battery and designed to operate within patient 12 for many months or years may be implanted.

Trial IMD 14 may be constructed to only include circuitry necessary to evaluate stimulation therapy. In one example, trial IMD 14 may include a secondary coil (not shown) configured to generate an electrical signal in response to a magnetic field generated by an external primary coil of powering device 20. The secondary coil may be a means for generating an electrical signal in response to a magnetic field. Trial IMD 14 may also include circuitry (e.g., a therapy module or filter module) configured to generate a stimulation signal in response to the electrical signal. The circuitry may be means for generating a stimulation signal in response to the electrical signal, such as rectification, conditioning, and control circuitry, e.g., as mentioned above. Trial IMD 14 may also include a non-hermetic implantable housing configured to encase the secondary coil and the circuitry.

Trial IMD 14 may also include, or be coupled with, lead 16 (e.g., an implantable medical lead or means for delivering the stimulation signal to patient 14). In one example, lead 16 may be configured to be removably coupled to the circuitry of trial IMD 14. Lead 16 may include a set of contacts configured to mate with a set of contacts within trial IMD 14. After the trial stimulation therapy, lead 16 may be removed from trial IMD 14 and electrically coupled with a chronic implantable medical device (e.g., a chronic neurostimulator). In this manner, lead 16 may be a chronic lead. Lead 16 switchable between trial IMD 14 and a chronic neurostimulator may allow lead 16 to remain in place if the trial stimulation therapy is successful. The electrodes of lead 16 used for trial and chronic stimulation may then be disposed at the same place such that chronic stimulation is more likely to be successful just as the trial stimulation. Not replacing lead 16 may also reduce potential damage to adjacent tissue.

In another example, trial IMD 14 may include a lead extension (not shown). The lead extension may be permanently coupled to the circuitry of trial IMD 14 and at least partially covered by the housing of trial IMD 14. In this manner, the lead extension may be configured to electrically couple the circuitry of trial IMD 14 to lead 16. The lead extension may allow trial IMD 14 to couple with a chronic lead 16 while minimizing the size of the housing with the connector to lead 16 outside of the housing.

In yet another example, trial IMD 14 may include lead 16 as a permanently coupled lead. Lead 16 may be permanently coupled to the circuitry of trial IMD 14 and at least partially covered by the housing. Lead 16 would then deliver the stimulation signal to patient 12. In this configuration, trial IMD 14 and lead 16 may be a single component implanted within patient 12. Although lead 16 may not remain within patient 12 after a successful trial period, the permanent lead 16 may allow trial IMD 14 to be constructed with a smaller size and with less cost. As used herein, permanently coupled may mean that one or more of the electrical conductors of lead 16 may be directly welded, soldered, or otherwise attached to the circuitry of trial IMD 14 without any removable connector that adds size and cost to trial IMD 14. In contrast, a removable connector may allow for a user to remove and replace the connection by using a set screw, friction fit, or other mechanism that does not affect the structural integrity of any structure.

The housing of trial IMD 14 may also be selected and constructed to minimize cost while allowing trial IMD 14 to be operational for the required trial period. This housing may be non-hermetic. In other words, a non-hermetic housing would not include a generally air-tight or water-tight housing of typical implantable medical devices. Typical implantable medical devices may include a housing constructed with a titanium alloy or other biocompatible material. This titanium alloy material may be used to construct a hermetic housing that prevents biological molecules from breaching the housing for extended periods of time, e.g., many years. However, hermetic housings such as titanium enclosures are expensive and not required for electrical components to operate within patient 14 for a few weeks or months. Therefore, the housing of trial IMD 14 may be a non-hermetic implantable housing constructed of biocompatible materials such as epoxy (e.g., polyepoxide) medical grade silicone gel or rubber, polyurethane, or other materials that at least minimally permeable. Although an epoxy, for example, may absorb water over time, the circuitry within the epoxy housing may be kept dry for the duration of the trial period. In other words, the epoxy housing may provide temporary moisture resistance and/or temporary resistance to molecules that may corrode elements of circuitry within trial IMD 14.

An epoxy, or other resin or polymer, may also allow for smaller circuitry within trial IMD 14. Materials used for a non-hermetic housing may be non-metallic. These non-metallic materials may attenuate magnetic fields from an external primary coil less than a metallic housing. Since the magnetic field may not be as attenuated with non-hermetic materials, a lower power may be used to sufficiently transfer power to trial IMD 14. Lower power needs may reduce the dimensions (e.g., diameter) of the secondary coil and/or number of windings of wire for the secondary coil within trial IMD 14. In addition, less heat may be generated during the power transfer from powering device 20 and trial IMD 14. In a metallic hermetic housing, current flow may be induced in the opposite direction of the secondary coil that generates heat. However, this current would not be generated in a non-hermetic housing that is electrically insulative.

The non-hermetic housing (e.g., an epoxy) may also allow for greater link efficiency between an external primary coil of powering device 20 and the secondary coil within trial IMD 14. Link efficiency may be described as the energy of the primary coil ($Q_P$) multiplied by the energy of the secondary coil ($Q_S$). For example, in a chronic neurostimulator with a titanium housing, the link efficiency between the primary and secondary coil may be approximately three percent. In comparison, the link efficiency between the primary and secondary coil may be approximately 25 percent with a non-hermetic housing comprised of epoxy or other non-metallic housing.

Generally, the non-hermetic housing may have a volume less than approximately 14.0 cubic centimeters. In one example, the non-hermetic housing may have a volume less than approximately 7.0 cubic centimeters. In another example, the non-hermetic housing may have a volume less than approximately 4.0 cubic centimeters. In still another example, the non-hermetic housing may have a volume less than approximately 2.0 cubic centimeters. Smaller volumes of the non-hermetic housing, and trial IMD 14, are preferred. However, the volume of the non-hermetic housing may be limited by the size of available circuitry necessary to provide the limited functions of trial IMD 14 described herein.

The material used for a non-hermetic housing may be a resin, polymer, or other material applied to circuitry of trial IMD 14 as a flowable material and solidifies to a more solid structure that retains its form, e.g., a moldable material. The flowable material may be a liquid or gel-like material that may be applied to the circuitry of trial IMD 14. After all of the circuitry, e.g., electrical components or modules, of trial IMD 14 are coupled, the flowable material may be applied or molded to the circuitry to encase or house each element of trial IMD 14. In other examples, the circuitry of trial IMD 14 may be dipped into the flowable material. Once the material solidifies, the solid housing may completely surround the circuitry of trial IMD 14. Alternatively, the material may be pre-formed into a mold, disposed around the circuitry, and then sealed with an adhesive or additional flowable material.

A non-hermetic housing may pass gasses, and even liquid molecules, at faster rates than hermetic housings traditionally used for implantable medical devices such as neurostimulators. The ability of a housing, or material protecting electrical components, may be measured based on the permeability of helium through the housing. Generally, the non-hermetic housing of trial IMD 14 may include a helium permeability greater than approximately $1\times10^{-8}$ cubic centimeters per second at zero degrees Celsius and one atmosphere pressure. A helium permeability of approximately $1\times10^{-8}$ cubic centimeters per second at zero degrees Celsius and one atmosphere pressure may be generally accepted as the threshold for a hermetic seal in implantable medical devices that limits the transfer of small molecules across the housing.

However, the housing of trail IMD 14 may be more permeable than the generally accepted hermetic housing and still protect circuitry within patient 12 for the trial period. In one example, the non-hermetic housing may comprise a helium permeability greater than approximately $1\times10^{-3}$ cubic centimeters per second at zero degrees Celsius and one atmosphere pressure. In another example, the non-hermetic housing may comprise a helium permeability greater than approximately 0.1 cubic centimeters per second at zero degrees Celsius and one atmosphere pressure. Therefore, a variety of materials may be used to construct the non-hermetic housing of trial IMD 14 and sufficiently protect circuitry for the trial period of time.

In some examples, the housing of trial IMD 14 may be more permeable to some molecules and less permeable to other molecules. For example, silicone may allow water to permeate the material while generally preventing ions and other modules to penetrate trial IMD 14. Even though water may come in contact with circuitry of trial IMD 14, corrosion may not occur as long as the circuitry is relatively free of ions after manufacturing. In this manner, a non-hermetic housing may allow some molecules to pass freely and other molecules to permeate at a much slower rate. The permeability for some non-hermetic materials may depend upon hydrophilic and hydrophobic properties, for example. In addition, the degree to which a housing is hermetic or non-hermetic may be determined using permeability tests other than Helium. In any case, a non-hermetic housing may be more permeable to most molecules than any hermetic housing used in chronic neurostimulators (e.g., a welded titanium housing).

The circuitry of trial IMD 14 may include several components. For example, the circuitry may include a power module configured to rectify or otherwise condition the electrical signal from an alternating current to a direct current. In some examples, this power module may include a full wave rectifier or a half wave rectifier. The power module or other rectifier circuit may be a means for rectifying the electrical signal from an alternating current to a direct current. In addition, trial IMD 14 may include a memory configured to store at least one set of trial stimulation therapy parameters that define the stimulation signal and a therapy module configured to generate the stimulation signal. The rectified electrical signal is configured to power the therapy module. These components may be included in trial IMD 14 when the stimulation signal is generated within trial IMD 14 and only power is received from powering device 20.

In another example, the circuitry of trial IMD 14 may include a filter module configured to output the stimulation signal when the electrical signal is applied to the filter module. The filter module and secondary coil may be the only components of trial IMD 14 when powering device 20 transmits the stimulation signal. Since the stimulation signal may be carried on a high-frequency carrier wave, the filter module may filter out the high-frequency carrier signal to generate the stimulation signal for trial stimulation therapy. In this example, trial IMD 14 may merely be an implantable receiver for stimulation signals generated by powering device 20.

Figure 2A:
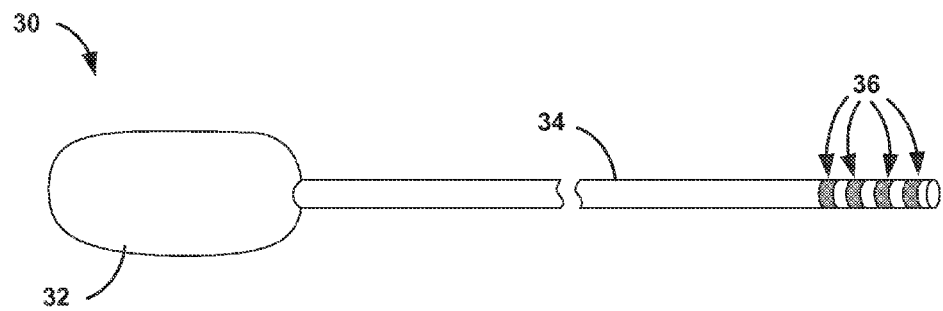
FIGS. 2A, 2B, and 2C are conceptual diagrams illustrating example trial neurostimulators and leads of FIG. 1.
Figure 2B:
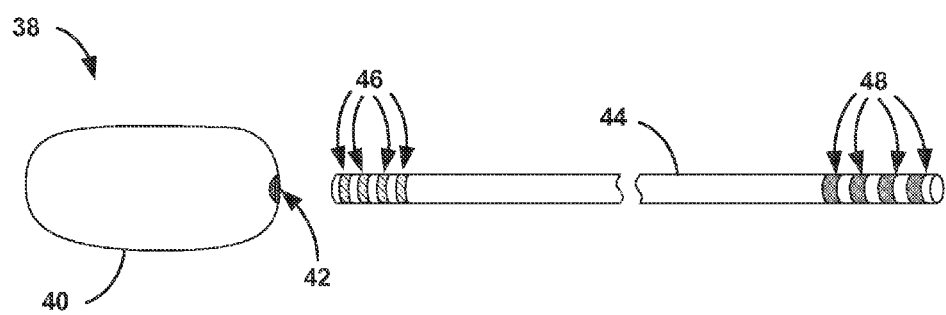
Figure 2C:
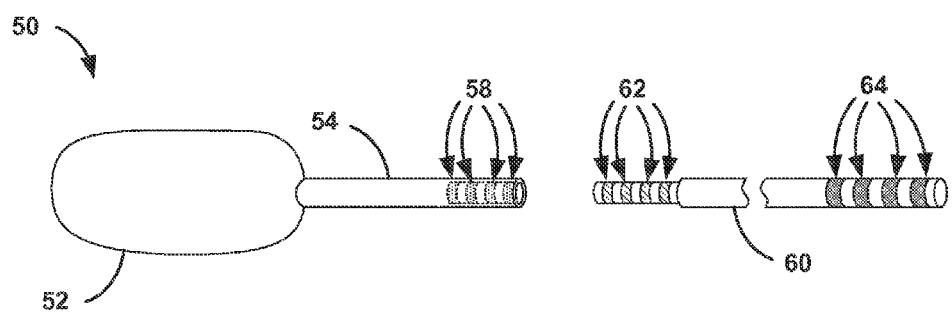

FIGS. 2A, 2B, and 2C are conceptual diagrams illustrating example trial IMDs and leads for trial stimulation therapy. Trial IMDs 32, 40, and 52 may be examples of trial IMD 14 of FIG. 1. Leads 34, 44, and 60 may be examples of lead 16. Although only one lead is generally described with each trial IMD, multiple leads may be coupled to each trial IMD in other examples. As shown in FIG. 2A, system 30 provides trial IMD 32 that is permanently coupled, or attached, to lead 34. Trial IMD 32 includes a non-hermetic housing that encases a secondary coil and circuitry for generating stimulation signals, processing and control circuitry, memory, and possibly telemetry circuitry. Lead 34 includes electrodes 36 disposed at a distal location along the lead. Electrodes 36 may be electrically coupled to conductors that reside within lead 34 and terminate within trial IMD 32. Lead 34 may include any number of electrodes (e.g., 2, 4, or 8 electrodes). The conductors of lead 34 are then permanently coupled to connectors within the housing of trial IMD 32. System 30 may then be implanted as a single unit for trial stimulation and removed as a single unit after the trial period is complete. Lead 34 is illustrated with a break to indicate that the length of lead 34 may be longer than illustrated in FIG. 2A.

Lead 34 may be permanently coupled to the circuitry (e.g., a therapy module) of trial IMD 32. The contacts or conductors at the proximal end of lead 34 may be soldered, welded, or otherwise electrically coupled to respective connectors within trial IMD 32. In addition, or instead of, the permanent electrical connection, at least a portion of lead 34 may be covered by the non-hermetic housing of trial IMD 32. A proximal end of lead 34 in proximity with the circuitry of trial IMD 32 may be covered or otherwise encased with the non-hermetic housing of trial IMD 32. Covering at least a portion of lead 34 may seal any gaps between lead 34 and trial IMD 32. In addition, the housing may retain lead 34 within trial IMD 32 when the housing adheres to the outer surface of lead 34.

As shown in FIG. 2B, system 38 provides trial IMD 40 that is removably coupled, or attached, to lead 44. Lead 44 may thus be electrically coupled with both trial IMD 40 and a chronic neurostimulator. Trial IMD 40 includes a non-hermetic housing that encases a secondary coil and circuitry for generating stimulation signals. Lead 44 includes electrodes 48 disposed at a distal location along the lead. Electrodes 48 may be electrically coupled to conductors that reside within lead 44 and terminate at contacts 46 on a proximal end of lead 44. Lead 44 may include any number of electrodes (e.g., 2, 4, or 8 electrodes). Contacts 46 of lead 44 may be configured on lead 44 such that each contact aligns with a respecting contact of the connector within slot 42 of trial IMD 40.

Contacts 46 of lead 44 and/or the housing of lead 44 may have a friction with within trial IMD 40 that keeps trial IMD 40 coupled with lead 44. Alternatively, one or more set screws, threaded structures of lead 44, or other attachment mechanism may be provided to prevent trial IMD 40 from being separated from lead 44 within patient 12. Lead 44 may be a chronic lead removably coupled to trial IMD 14 for trial stimulation therapy. After a successful trial stimulation, lead 44 may remain implanted within patient 12 and coupled to a chronic neurostimulator. Lead 44 is illustrated with a break to indicate that the length of lead 44 may be longer than illustrated in FIG. 2B.

Lead 44 may be removably coupled to the circuitry (e.g., a therapy module) of trial IMD 40. The contacts at the proximal end of lead 44 may be in electrical contact with respective contacts within slot 42 of trial IMD 40. In some examples, trial IMD 40 may include a header or other connector configured to couple with contacts 46 of lead 44. Although the non-hermetic housing may not be adhered or otherwise formed around lead 44, the housing may be shaped such the housing contacts lead 44 around the entire circumference of lead 44 to prevent body fluids from entering trial IMD 40. Alternatively, trial IMD 40 or lead 44 include an o-ring or other seal around the connection of lead 44 with trial IMD 40. After the trial stimulation therapy is complete, trial IMD 40 may be disposed.

As shown in FIG. 2C, system 50 includes trial IMD 52 permanently coupled, or attached, to lead extension 54. Lead 60 may then be removably coupled to lead extension 54. In this manner, lead extension 54 may be configured to electrically couple the circuitry of trial IMD 52 to lad 60. Trial IMD 52 includes a non-hermetic housing that encases a secondary coil and circuitry for generating stimulation signals. Lead 60 includes electrodes 64 disposed at a distal location along the lead. Electrodes 64 may be electrically coupled to conductors that reside within lead 60 and terminate at contacts 62. Lead 60 may include any number of electrodes (e.g., 2, 4, or 8 electrodes).

Contacts 62 of lead 60 are then configured to removably couple with respective contacts 58 within lead extension 54. When coupled, lead 60 and lead extension 54 may create a fluid tight seal to protect contacts 58 and 62. System 50 may be used to provide trial stimulation therapy. Lead 60 is illustrated with a break to indicate that the length of lead 60 may be longer than illustrated in FIG. 2C. After successful trial stimulation, lead 60 may be removed from lead extension 54 and coupled to a chronic neurostimulator and/or lead extension. The conductors of lead extension 54 may be permanently coupled to connectors or other circuitry within the housing of trial IMD 52. Therefore, both trial IMD 52 and lead extension 54 may be removed from patient 12 after a successful trial stimulation and replaced with a chronic neurostimulator. However, lead 60 may be left implanted in the patient for connection with a subsequently implanted chronic neurostimulator.

Lead extension 54 may be permanently coupled to the circuitry (e.g., a therapy module) of trial IMD 52. The contacts or conductors at the proximal end of lead extension 54 may be soldered, welded, or otherwise electrically coupled to respective connectors within trial IMD 52. In addition, or instead of, the permanent electrical connection, at least a portion of lead extension 54 may be covered by the non-hermetic housing of trial IMD 52. A proximal end of lead extension 54 in proximity with the circuitry of trial IMD 52 may be covered or otherwise encased with the non-hermetic housing of trial IMD 52. Covering at least a portion of lead extension 54 may seal any gaps between lead extension 54 and trial IMD 52. In addition, the housing may retain lead 54 within trial IMD 52 when the housing adheres to the outer surface of lead extension 54.

Systems 39, 38, and 50 illustrate example trial IMDs and leads that may be provided in accordance with the techniques described herein. Other examples of trial IMDs may include differently shaped trial IMD housings, alternative connections between the trial IMD and the lead, three or more lead segments, or other variations. In any case, the circuitry of the trial IMD may be encased in a non-hermetic implantable housing. In addition, the trial IMD may be permanently coupled to the lead or removably coupled to the lead.

Figure 3A:
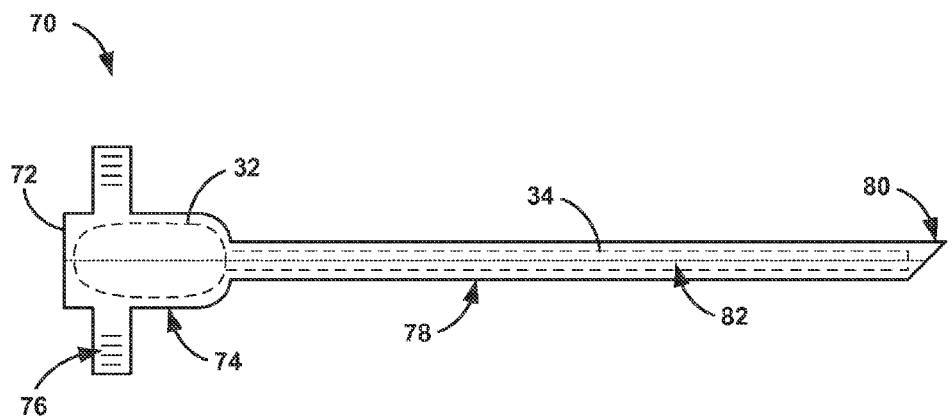
FIGS. 3A and 3B are conceptual diagrams illustrating an example introducer for implanting the trial neurostimulator of FIG. 1.
Figure 3B:
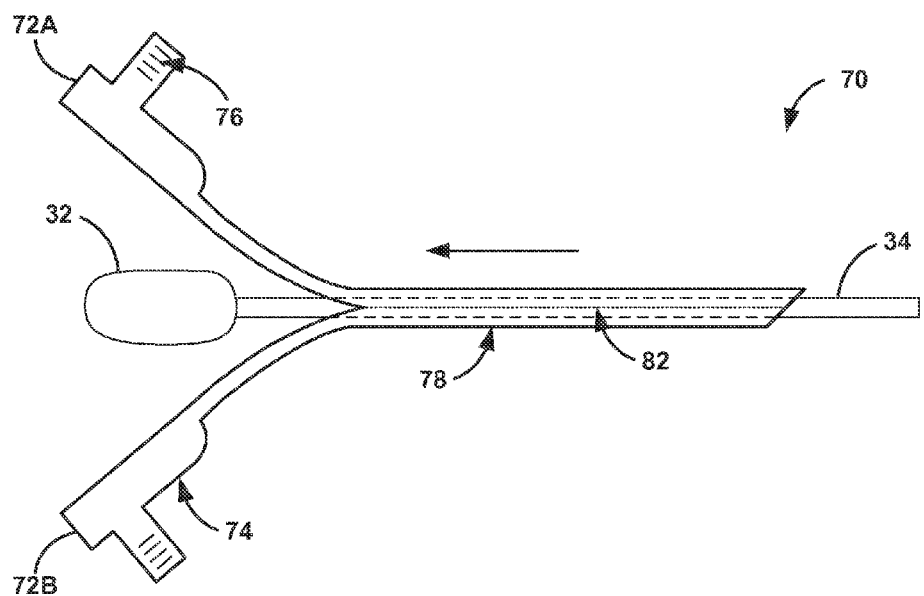

FIGS. 3A and 3B are conceptual diagrams illustrating an example introducer 72 for implanting a trial IMD and coupled lead. Introducer 72 may be used with any of Trial IMDs 14, 32, 40, and 52 and leads 16, 34, 44, and 60 described herein. However, IMD 32 and permanently coupled lead 34 will be described for illustrative purposes. System 70 may include introducer 72, trial IMD 32, and lead 34. When trial IMD 32 is permanently coupled to lead 34, typically introducers that aid in the implantation of lead 34 may be prevented from being removed from lead 34. Introducers may be constructed of a more rigid material than lead 34 and/or provide the ability to steer lead 34 within patient 12. Since the housing of trial IMD 32 may have a larger diameter than lead 34, the sheath disposed over lead 34 cannot be slid past trial IMD 32 and removed from lead 34 after lead 34 is disposed at the desired anatomical location. Therefore, introducer 72 may be splittable, or separable, to allow introducer 72 to be removed from patient 12.

As shown in FIG. 3A, introducer 72 includes housing portion 74, handles 76, sheath 78, tip 80, and longitudinal score 82 within sheath 78. Trial IMD 32 may include lead 34 and reside completely within introducer 72. In other examples, the housing of trial IMD 32 may be reside at least partially external to introducer 72. In the closed configuration of introducer 72 illustrated in FIG. 3A, introducer 72 may be configured to aid a clinician in implanting trial IMD 32 and lead 34 into patient 12.

Sheath 78 may be configured to accept at least a portion of lead 34, although FIG. 3A illustrates that sheath 78 is configured to accept the entire length of lead 34. Sheath 78 may have a greater stiffness than lead 34 such that sheath 78 can be pushed into tissue with minimal deformation. In addition, sheath 78 includes at least one structural characteristic (e.g., longitudinal score 82) configured to facilitate splitting sheath 78 along a length of the sheath. In other words, longitudinal score 82 may be a structural characteristic or deficiency that enables the user to separate sheath 78 along the structural characteristic. Longitudinal score 82 may run the entire length of introducer 72. By splitting sheath 78 along the longitudinal length of the sheath, the user may remove sheath 78 past the larger housing of trial IMD 32. In other examples, the structural characteristic may be a perforation, pre-stressed section, or other structure that enables sheath 78 to be removed.

Introducer 72 also includes handles 76. Handles 76 may be configured to separate sheath 78 along the at least one structural characteristic (e.g., longitudinal score 82) in response to a force directed away from trial IMD 32. In other words, the clinician may grab each of handles 76 and pull handles 76 apart to remove introducer 78 from lead 34. Force from the user may cause introducer 72 to separate along longitudinal score 82 (e.g., a thin region of introducer 72.

As shown in FIG. 3B, a user has applied opposing forces to handles 76 to pull introducer half 72A from introducer half 72B. As the user keeps pulling handles 76 apart and in the direction of the arrow, the user may fully remove introducer 72 from trial IMD 32 and lead 34. This splitting action may be performed while lead 34 remains implanted at the desired location within patient 12. In other examples, introducer 72 may only cover a portion of trial IMD 32 or only lead 34. Alternative to a structural characteristic of sheath 78 that facilitates removal of introducer 72, the user may remove introducer 72 using a cutting tool or other such device.

Figure 4:
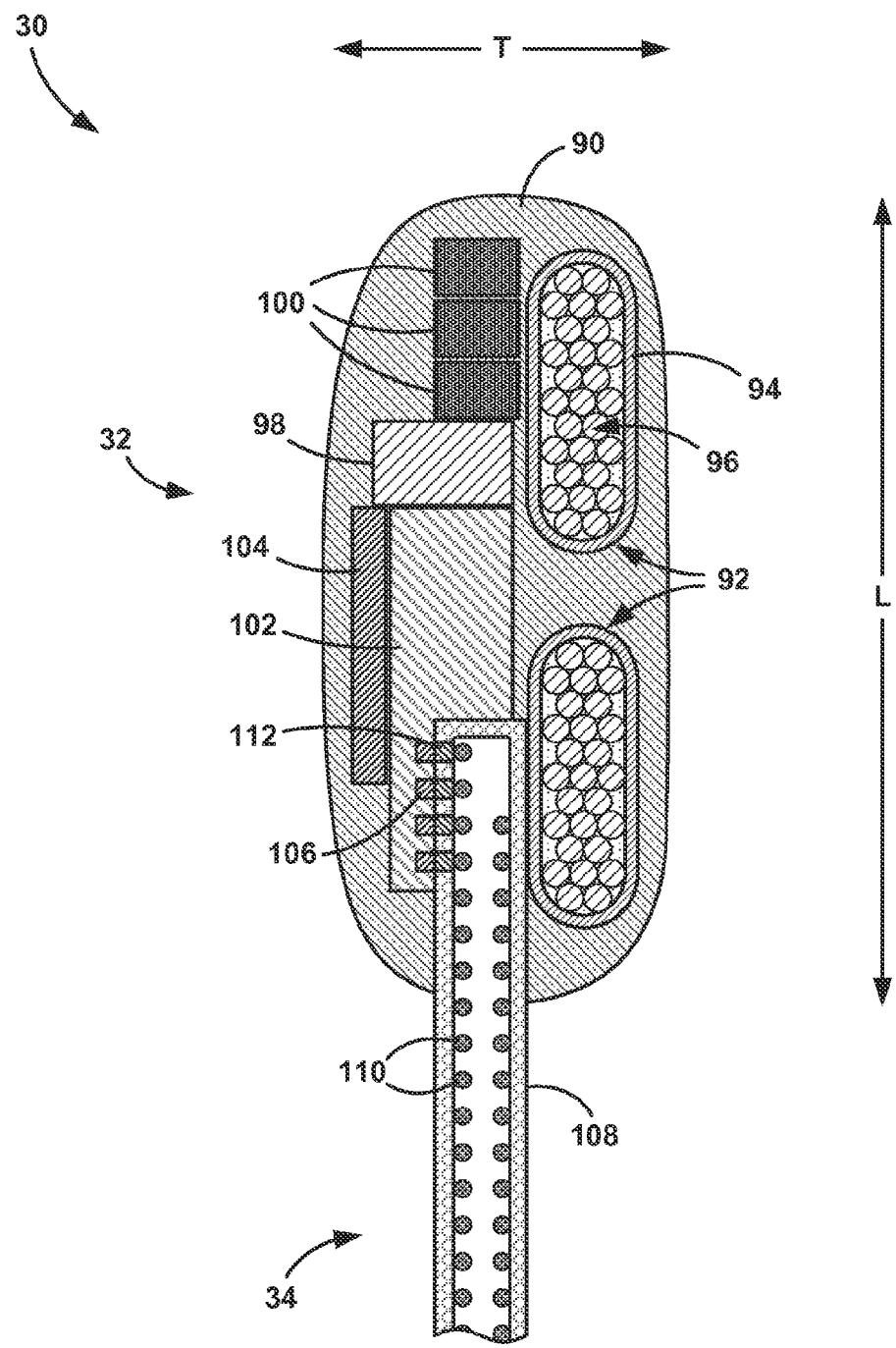
FIG. 4 is a cross-sectional illustration of an example trial neurostimulator and lead.

FIG. 4 is a cross-sectional illustration of example trial IMD 32 and lead 34. Although trial IMD 32 and lead 34 are used as an example in FIG. 4, other trial IMDs and leads may include similar components. As shown in FIG. 4, system 30 includes IMD 32 permanently coupled to lead 34. Trial IMD 32 includes secondary coil 92, power module 98, capacitors 100, therapy module 102, memory 104, and contacts 106. Lead 34 includes elongated housing 108, conductors 110, and contacts 112. Housing 90 of trial IMD 32 is a non-hermetic housing that encases the components of trial IMD 32 and a proximal portion of lead 34. The circuitry (e.g., capacitors 100, power module 98, therapy module 102, and memory 104) of trial IMD 32 may be arranged in different positions, have different shapes, or have different sizes in other examples.

Secondary coil 92 may be shaped as a disk with a hole in the middle of the disk. Secondary coil 92 may include an insulated coil 96 wound a plurality of times within the disk (e.g., a spiral wound wire). Although secondary coil 92 may include multiple layers of coil 96, secondary coil 92 may include a single layer of a spiral wound coil in other examples. Secondary coil 92 may also include coil housing 94 that encases insulated coil 96. Insulated coil 96 may be an electrically conductive wire covered in an electrically insulating sheath. In other examples, housing 90 may be the only housing the encases insulated coil 96. Secondary coil 92 may include the necessary windings of wire 96 to receive power from powering device 20. The current induced in secondary coil 92 may be rectified or transformed by power module 98 and briefly stored in capacitors 100 to maintain the level of operating power for therapy module 102. Therapy module 102 may then generate stimulation signals based on parameters stored in memory 104 Power module 98 may include suitable circuitry for generating and regulating appropriate voltages and/or currents to support control, processing and generation of stimulation signals. Memory 102 may be pre-stored with one or more sets of trial stimulation parameters. In other examples, powering device 20 or a programmer may modify the stored trial stimulation parameters. The stimulation signals are then transferred to conductors 110 via contacts 106 and 112 to the delivered to patient 12.

Non-hermetic housing 90 may encase or otherwise protect the components of trial IMD 32 from biological substances for the duration of the trial period. Housing 90 may be constructed of numerous materials that may be biocompatible be also considered non-hermetic because the materials are too permeable to gasses and fluids. Example materials may include epoxy (e.g., polyepoxide) and silicone. These materials may be formed over the circuitry and other components within trial IMD 32. The materials may be applied to the components with a spray or the components may be dipped into the materials when flowable or otherwise moldable. The material of housing 90 may then be deposited around each component and may be disposed between two or more components within trial IMD 32 (e.g., a portion of housing 90 may be disposed between therapy module 102 and secondary coil 92. The materials may then solidify to form a solid and non-flowable housing 90. In this manner, housing 90 may be disposed around and within different components of trial IMD 32. Alternatively, the components of trial IMD 32 may be packed within an insulating material and then covered with the material of housing 90. Housing 90 may be formed with one or more layers of material.

Further, housing 90 may be injection molded with polyurethane or other moldable material. This injection mold may or may not be filled with silicone or epoxy material in contact with the circuitry. In this manner, housing 90 may include two or more layers of material. These different materials may provide a different hardness (e.g., as measured by a durometer) for placement adjacent certain anatomical structures or to promote patient comfort. For example, the outer material may be a lower hardness such that trial IMD 32 feels at least someone deformable to patient 12. The inner material may then have a higher hardness to keep circuitry in specific locations of trial IMD 32.

The dimensions of housing 90 may be relatively small compared to typical implantable medical devices. Since trial IMD 32 may be designed to be functional for a short period of time, trial IMD 32 may only include a limited number of components or circuitry. Large components, such as a battery, would not be present in trial IMD 32. Housing 90 may generally have a length L less than approximately 50 millimeters (mm). More specifically, housing 90 may have a length L less than approximately 20 mm. Housing 90 may also have a thickness T generally less than approximately 20 mm. More specifically, housing 90 may have a thickness T less than approximately 7.0 mm. Housing 90 may also have a width (not shown) generally less than approximately 50 millimeters (mm). More specifically, housing 90 may have a width less than approximately 20 mm.

Since housing 90 may have a shape with various surfaces and dimensions (e.g., housing 90 may be amorphous due to molding, dipping, or coating techniques), it may be more appropriate to describe housing 90 by volume. The volume of housing 90 is described as the entire volume within and including the outer surface of housing 90. In other words, the volume of housing 90 is not merely the volume of the material used to form housing 90. Generally, the non-hermetic housing may have a volume less than approximately 14.0 cubic centimeters. In one example, the non-hermetic housing may have a volume less than approximately 7.0 cubic centimeters. In another example, the non-hermetic housing may have a volume less than approximately 4.0 cubic centimeters. In still another example, the non-hermetic housing may have a volume less than approximately 2.0 cubic centimeters.

Non-hermetic housing 90 may pass gasses, and even liquid molecules, at faster rates than hermetic housings traditionally used for implantable medical devices such as neurostimulators. The ability of a housing or material to protect electrical components may be measured based on the permeability of helium through the housing. Generally, the non-hermetic housing of trial IMD 14 may include a helium permeability greater than approximately $1\times10^{-8}$ cubic centimeters per second at zero degrees Celsius and one atmosphere pressure. In other words, a hermetic housing may have a helium permeability less than approximately $1\times10^{-8}$ cubic centimeters per second at zero degrees Celsius and one atmosphere pressure. This helium permeability of approximately $1\times10^{-8}$ cubic centimeters per second at zero degrees Celsius and one atmosphere pressure may be generally accepted as the threshold for a hermetic seal in implantable medical devices.

However, the housing of trail IMD 32 may be more permeable than the generally accepted hermetic housing and still protect circuitry within patient 12 for the trial period. In one example, the non-hermetic housing may comprise a helium permeability greater than approximately $1\times10^{-3}$ cubic centimeters per second at zero degrees Celsius and one atmosphere pressure. In another example, the non-hermetic housing may comprise a helium permeability greater than approximately 0.1 cubic centimeters per second at zero degrees Celsius and one atmosphere pressure. Therefore, a variety of materials may be used to construct the non-hermetic housing of trial IMD 14 and sufficiently protect circuitry for the trial period of time.

Since some molecules within patient 12 would pass through housing 90, housing 90 may be considered non-hermetic. In some example, housing 90 may absorb water or other molecules over time. This absorption may lead to structural degradation of housing 90. However, this degradation of housing 90 may be insufficient to damage circuitry within trial IMD 32 or expose patient 12 any foreign compounds. In this manner, housing 90 with an example epoxy housing 90 may be less hermetic than the housing of chronic devices which include welded titanium. In some examples, the non-hermetic housing is substantially less hermetic than chronic housings. Accordingly, a housing may not be hermetic or non-hermetic based on one specific permeability rating. Instead, the housing may be less hermetic as the housing is constructed to be more permeable to molecules in the body. Housing 90 may not be constructed with the goal of a certain permeability. Materials and dimensions for housing 90 may be instead selected to minimize cost and volume of trial IMD 32. These materials and dimensions may result in a less hermetic housing than would be acceptable in chronic devices, but the housing may be sufficiently resistant for trial IMD 32 operation during the relatively short trial period.

Figure 5A:
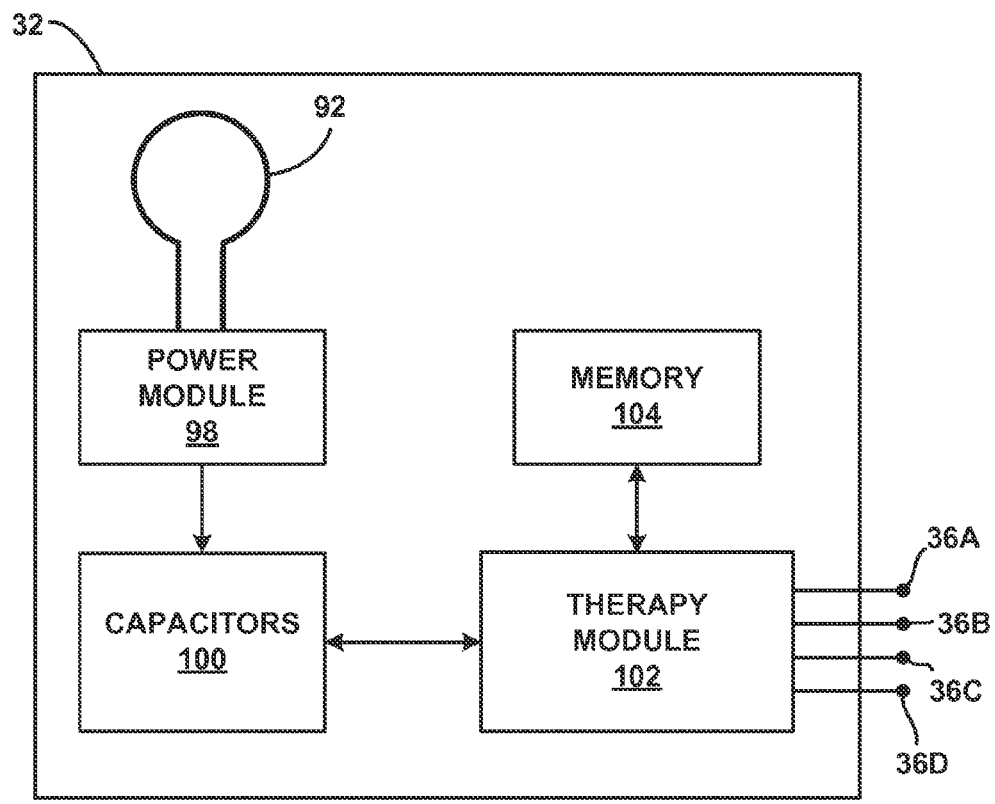
FIG. 5A is a block diagram of the example trial neurostimulator of FIG. 4.

FIG. 5A is a block diagram of the example trial IMD 32 of FIG. 4. Although the components of FIG. 5A are described with respect to trial IMD 32, these components may also be provided within any other trial IMDs such as trial IMDs 14, 40, and 52. In the example of FIG. 5A, IMD 32 includes coil 92, power module 98, capacitors 100, therapy module 102, and memory 104. Trial IMD 32 does not include a battery or other power storage device. In addition, therapy module 102 may include one or more processors configured to perform the operations needed to generate and deliver trial stimulation signals to patient 12. In other examples, trial IMD 32 may include a greater or fewer number of components. For example, in some examples, trial IMD 32 may not include a separate memory 104 and/or capacitors 100. In other examples, capacitors 100 may be formed as part of power module 98 or therapy module 102. In addition, trial IMD 32 may include signal conditional and regulating circuitry separate or as a part of therapy module 102.

In general, trial IMD 32 may comprise any suitable arrangement of hardware, alone or in combination with software and/or firmware, to perform the various techniques described herein attributed to trial IMD 32 and therapy module 102 (e.g., generate trial stimulation signals when power is received by coil 92). In various examples, trial IMD 32 may include one or more processors or other control hardware within therapy module 102, such as one or more microprocessors, digital signal processors (DSPs), application specific integrated circuits (ASICs), field programmable gate arrays (FPGAs), or any other equivalent integrated or discrete logic circuitry, as well as any combinations of such components. However, trial IMD 32 may include control hardware separate from therapy module 102. Trial IMD 32 also, in various examples, may include a memory 104, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although therapy module 102, memory 104, and power module 98 are described as separate modules, in some examples, therapy module 102, memory 104, and power module 98 are functionally integrated. In other examples, therapy module 102, memory 104, and power module 98 may correspond to individual hardware units, such as ASICs, DSPs, FPGAs, or other hardware units. In any event, power module 98, capacitors 100, therapy module 102, memory 104, and any other provided data bus or supporting hardware may be described as circuitry within trial IMD 32. Although trial IMD 32 is not shown as including telemetry circuitry, alternative examples of trial IMD 32 may also include circuitry that supports wireless telemetry with external devices (e.g., an external programmer).

Memory 104 may store therapy programs or other instructions that specify therapy parameter values for the trial stimulation therapy provided by therapy module 102 and IMD 32. In some examples, memory 104 may also store instructions for transforming, rectifying, or filtering the electrical signal induced in coil 92, or any other instructions required to perform tasks attributed to IMD 32. However, the functions provided by therapy module 102 and memory 104 may be limited to those required to deliver trial stimulation therapy during the trial period. This limited function may allow therapy module 102 and memory 104, for example, to be constructed with minimal circuitry requiring a small volume of space within trial IMD 32. The trial period may be a relatively short duration of time selected to evaluate the efficacy of electrical stimulation therapy. This trial period may be on the order of a few days, weeks, or perhaps months, as compared with chronic therapy delivered over several years. In one example, the trial period may be less than approximately eight weeks. In another example, the trial period may be less than approximately four weeks. In any example, the length of the trial period may be limited by the time the housing of trial IMD 32 can remain function within patient 12.

Generally, therapy module 102 may generate and deliver electrical stimulation under the control of an included processor or similar circuitry. In some examples, therapy module 102 may access memory 104 to selectively access and load at least one of the trial stimulation programs to therapy module 102. For example, in operation, therapy module 102 may access memory 104 to load one of the stimulation programs to therapy module 102. One or more sets of stimulation parameters that define trial stimulation therapy may be selected to emulate or otherwise evaluate likely chronic stimulation therapy. In such examples, relevant stimulation parameters may include a voltage amplitude, a current amplitude, a pulse rate, a pulse width, a duty cycle, or the combination of electrodes 36A, 36B, 36C, and 36D that therapy module 102 uses to deliver the electrical stimulation signal. Although therapy module 102 may be configured to generate and deliver electrical stimulation therapy via one or more of electrodes 36A, 36B, 36C, and 36D of lead 16, therapy module 102 may be configured to provide different therapy to patient 12. For example, therapy module 102 may be configured to deliver drug delivery therapy via a catheter during a trial period. These and other therapies may be provided by trial IMD 32.

Trial IMD 23 also includes components to receive power from charging device 20 to operate therapy module 102 and generate trial stimulation signals. Coil 92 may be a secondary coil coupled to power module 98. Power module 98 may be configured to transform, rectify, and/or filter, or otherwise condition, the electrical signal induced in coil 92 from the external primary coil during inductive coupling.

Secondary coil 92 may include a coil of wire or other device capable of inductive coupling with a primary coil disposed external to patient 12. Although coil 92 is illustrated as a simple loop of in FIG. 5A, secondary coil 92 may include multiple turns of wire. Coil 92 may include a winding of wire configured such that an electrical current can be induced within coil 92 from a magnetic field. The induced electrical current may then be used to provide an electrical signal configured to power therapy module 102, for example. The coupling between coil 92 and the primary coil of powering device 20 may be dependent upon the alignment of the two coils. Generally, the coupling efficiency increases when the two coils share a common axis and are in close proximity to each other. Powering device 20 and/or trial IMD 32 may provide one or more audible tones or visual indications of the alignment. Although inductive coupling is generally described as the method for powering trial IMD 32, other wireless energy transfer techniques may alternatively be used.

Power module 98 may include one or more circuits that filter and/or transform the electrical signal induced in coil 92 to an electrical signal capable of powering the circuitry of trial IMD 32. For example, in alternating current induction, power module 98 may include a half-wave rectifier circuit and/or a full-wave rectifier circuit configured to convert alternating current from the induction to a direct current for operational power. The full-wave rectifier circuit may be more efficient at converting the induced energy from coil 92. However, a half-wave rectifier circuit may be used to generate lower voltage and/or current, or voltage and/or current with lower efficiency. In some examples, power module 98 may include both a full-wave rectifier circuit and a half-wave rectifier circuit such that power module 98 may switch between each circuit to control the amount of power received by trial IMD 32.

Power module 98 may transmit the received electrical signal to capacitors 100. Capacitors 100 may temporarily store power for operation of therapy module 102. This storage of power is merely temporary and may not allow trial IMD 32 to function for any appreciable amount of time without receiving power via coil 92. Instead, capacitors 100 may allow trial IMD 32 to maintain operational power for brief periods of time due to temporary misalignment between coil 92 and the external primary coil. In addition, capacitors 100 may manage fluctuations in the voltage received from power module 98.

In this manner, power module 98 of trial IMD 32 may be configured to rectify the electrical signal from the alternating current induced in coil 92 to a direct current usable by therapy module 102. A rectified electrical signal from power module 98, for example, may be configured to power therapy module 102. Trial IMD 32 may be constructed with smaller dimensions and at a lower cost than typical medical devices including a battery trial stimulation therapy.

Figure 5B:
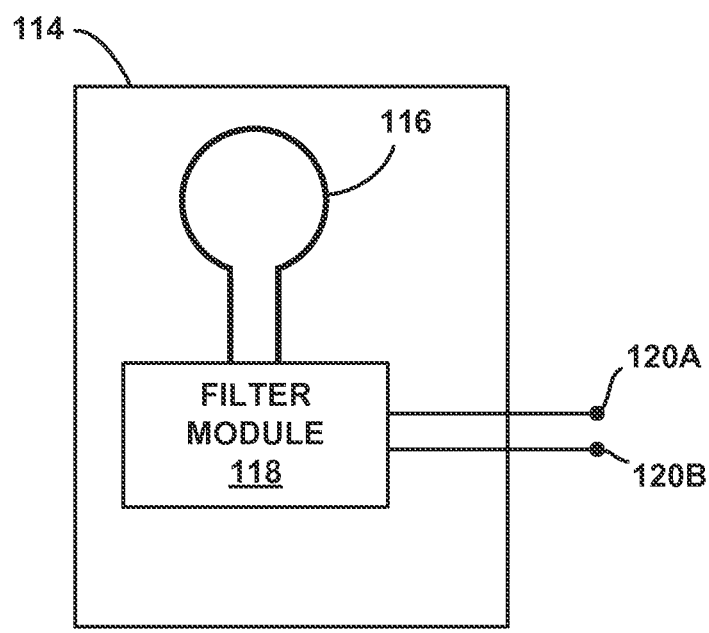
FIG. 5B is a block diagram of an alternative trial neurostimulator.

FIG. 5B is a block diagram of an alternative trial IMD 114. Trial IMD 114 may be an example of trial IMD 14 and may be similar to any of trial IMDs 32, 40, and 52. However, trial IMD 114 is configured to receive a transferred signal from an external primary coil and generate the trial stimulation signal directly from the received signal. In the example of FIG. 5B, trial IMD 114 includes coil 116 and filter module 118. Coil 116 may be a secondary coil similar to coil 92 of FIG. 5A. Filter module 118 may include one or more analog or digital filters that generate the trial stimulation signal directly from the induced electrical signal in coil 116. This minimal componentry of trial IMD 114 may allow trial IMD 114 to be constructed with minimal size and at a minimal cost.

The circuitry of trial IMD 114 includes filter module 118 configured to output the stimulation signal when the electrical signal received by coil 116 is applied to filer module 118. The electrical signal induced in coil 116 may be received by filter module 118. The electrical signal may include a low frequency stimulation signal contained within a high-frequency carrier wave. This high-frequency carrier wave may be needed to drive the signal wirelessly between the external primary coil and the implanted secondary coil 116. Filter module 118 may include one or more low-pass filters, for example, to extract the low frequency signal that is the trial stimulation signal. In this manner, powering device 20 may generate and drive the trial stimulation signal through the skin of patient 12. Powering device 20 may thus contain a therapy module and memory to generate stimulation signals according to a set of trial stimulation parameters.

In some examples, filter module 118 may include a power module and/or one or more amplifiers used to condition the trial stimulation signal into a signal appropriate for delivery to patient 12. In any case, the circuitry of trial IMD 114 is minimal such that the size and cost of trial IMD 114 may be minimized. Therefore, trial IMD 114 may be constructed smaller and more inexpensively than even trial IMD 32 of FIG. 5B.

Figure 6:
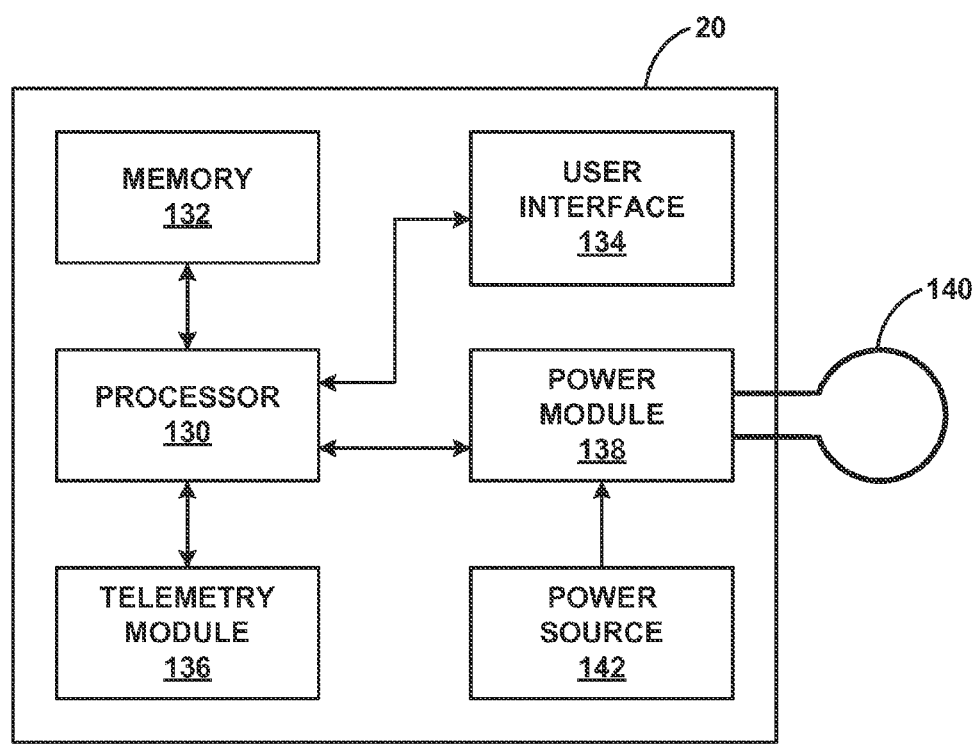
FIG. 6 is a block diagram of the example external powering device of FIG. 1.

FIG. 6 is a block diagram of the example external powering device 20. While powering device 20 may generally be described as a hand-held device, powering device 20 may be a larger portable device or a more stationary device. In addition, in other examples, powering device 20 may be included as part of an external programmer or include functionality of an external programmer. In addition, powering device 20 may be configured to communicate with an external programmer. As illustrated in FIG. 6, powering device 20 may include a processor 130, memory 132, user interface 134, telemetry module 136, power module 138, coil 140, and power source 142. Memory 132 may store instructions that, when executed by processor 130, cause processor 130 and external powering device 20 to provide the functionality ascribed to external powering device 20 throughout this disclosure.

In general, powering device 20 comprises any suitable arrangement of hardware, alone or in combination with software and/or firmware, to perform the techniques attributed to powering device 20, and processor 130, user interface 134, telemetry module 136, and power module 138 of powering device 20. In various examples, powering device 20 may include one or more processors, such as one or more microprocessors, DSPs, ASICs, FPGAs, or any other equivalent integrated or discrete logic circuitry, as well as any combinations of such components. Powering device 20 also, in various examples, may include a memory 132, such as RAM, ROM, PROM, EPROM, EEPROM, flash memory, a hard disk, a CD-ROM, comprising executable instructions for causing the one or more processors to perform the actions attributed to them. Moreover, although processor 130 and telemetry module 136 are described as separate modules, in some examples, processor 130 and telemetry module 136 are functionally integrated. In some examples, processor 130 and telemetry module 136 and power module 138 correspond to individual hardware units, such as ASICs, DSPs, FPGAs, or other hardware units.

Memory 132 may store instructions that, when executed by processor 130, cause processor 130 and powering device 20 to provide the functionality ascribed to powering device 20 throughout this disclosure. For example memory 132 may include instructions that cause processor 130 to initiating transmission of power to trial IMD 14, for example, via coil 140. In some examples, memory 132 may include one or more sets of trial stimulation parameters used to generate a stimulation signal by power module 138 and transmitted to trial IMD 114. In addition, memory 132 may store a log of how and when power module 138 transmitted power to trial IMD 14. Processor 130 may, when requested, transmit any of this stored data in memory 132 to another computing device for review or further processing. For example, powering device 20 may be in communication with another programming device (e.g., a patient or clinician programmer used to communicate with a chronic neurostimulator).

User interface 134 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 130 may present and receive information relating to the transmission of power to trial IMD 14 via user interface 134. For example, user interface 134 may indicate when power transmission is occurring, quality of the alignment between coils 140 and 92, the duration of power transmission, the amount of time powering device 20 was not transmitting power, or any other information.

User interface 134 may also receive user input via user interface 134. The input may be, for example, in the form of pressing a button on a keypad or selecting an icon from a touch screen. The input may request starting or stopping a trial stimulation session. In this manner, user interface 134 may allow the user to view information related to the powering of trial IMD 14. In alternative examples, user interface 134 may be a minimal power toggle that turns the transmission of power to trial IMD 14 on and off.

Powering device 20 also includes components to transmit power to trial IMD 14. As shown in FIG. 6, powering device 20 includes primary coil 140 and power module 138 coupled to power source 142. Power module 138 may be configured to generate an electrical current in primary coil 140 from voltage stored in power source 142. Although primary coil 140 is illustrated as a simple loop of in FIG. 6, primary coil 140 may include multiple turns of wire. Power module 138 may generate the electrical current according to a power level selected by processor 130 based on the type of circuitry (e.g., secondary coil and voltage requirements of components) of trial IMD 14.

Primary coil 140 may include a coil of wire, e.g., having multiple turns, or other device capable of inductive coupling with a secondary coil 92 disposed within patient 12. Primary coil 140 may include a winding of wire, e.g., with multiple turns, configured such that an electrical current generated within primary coil 140 can produce a magnetic field configured to induce an electrical current within secondary coil 92. The induced electrical current in coil 92 may then be used to power circuitry within trial IMD 14. The coupling efficiency between primary coil 140 and secondary coil 92 may be dependent upon the alignment of the two coils. Generally, the coupling efficiency increases when the two coils share a common axis and are in close proximity to each other. User interface 134 of powering device 20 may provide one or more audible tones or visual indications of the alignment.

Power module 138 may include one or more circuits that generate an electrical signal, and an electrical current, within primary coil 140. Power module 138 may generate an alternating current of specified amplitude and frequency in some examples. In other examples, power module 138 may generate a direct current. In any case, power module 138 may be capable of generating electrical signals, and subsequent magnetic fields, to transmit power to trial IMD 14.

In one example, power module 138 may generate a magnetic field external to patient 12 with coil 140. The electrical parameters that define the magnetic field may be selected to transmit operating power to circuitry within trial IMD 14. In another example, power module 138 may be configured to generate a transmission signal with coil 140 that includes a trial stimulation signal usable by trial IMD 14 to deliver therapy. Power module 138 may generate a magnetic field from electrical parameters that define the magnetic field and selected to induce an electrical signal in a secondary coil that contains the simulation signal. In this example, power module 138 may apply the stimulation signal to a high-frequency carrier wave so that power module 138 may drive the stimulation signal through the skin of patient 12 via coil 140.

Power source 142 may deliver operating power to the components of powering device 20. Power source 142 may also deliver the operating power to drive primary coil 140 during the charging process. Power source 142 may include a battery and a power generation circuit to produce the operating power. In some examples, the battery may be rechargeable to allow extended portable operation. In other examples, power source 142 may draw power from a wired voltage source such as a consumer or commercial power outlet.

Although power source 142, power module 138 are shown within a housing of powering device 20 and primary coil 140 is shown external to powering device 20, different configurations may also be used. For example, primary coil 140 may also be disposed within the housing of powering device 20. In another example, power source 142, power module 138, and primary coil 140 may be all located external to the housing of powering device 20 and coupled to powering device 20.

Telemetry module 136 may support wireless communication between powering device 20 and another device (e.g., an external programmer) under the control of processor 130. Telemetry module 136 may also be configured to communicate via wireless communication techniques or direct communication through a wired connection. For example, telemetry module 136 may be configured to conduct wireless communication with another device using radio frequency, inductive coupling, or any other techniques commonly used in the medical arts. In some examples, telemetry module 136 may include an antenna, which may take on a variety of forms, such as an internal or external antenna.

Examples of local wireless communication techniques that may be employed to facilitate communication between powering device 20 and IMD 14 include RF communication according to the 802.11 or Bluetooth specification sets or other standard or proprietary telemetry protocols. In this manner, other external devices may be capable of communicating with powering device 20 without needing to establish a secure wireless connection.

Figure 7:
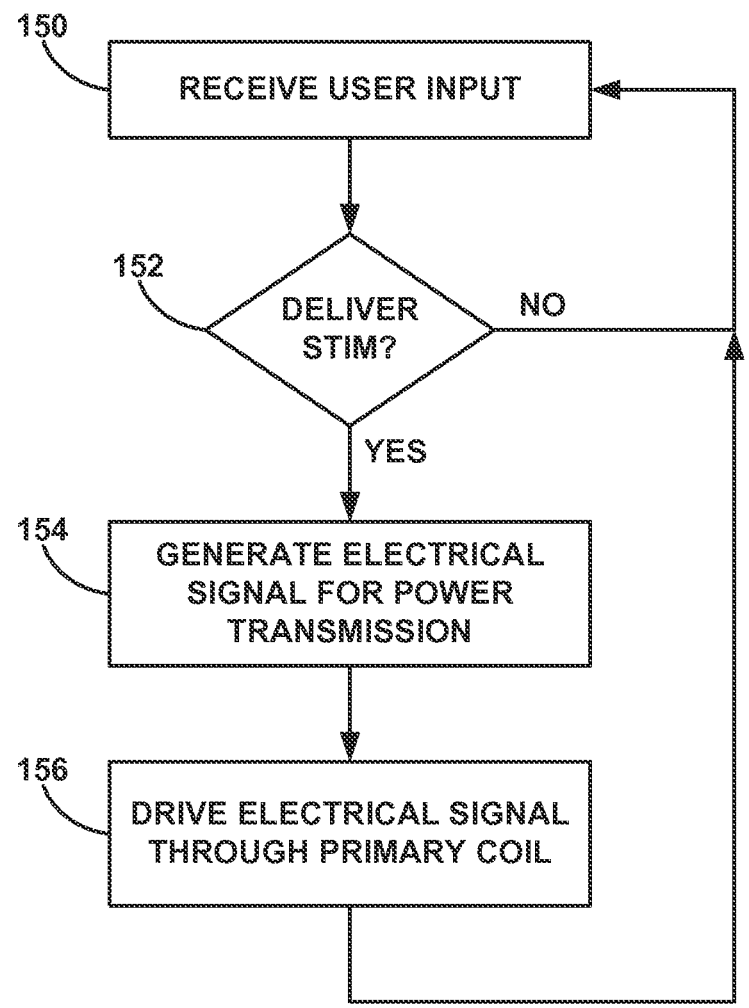
FIG. 7 is a flow diagram illustrating an example technique for providing operational power to an implantable trial neurostimulator.

FIG. 7 is a flow diagram illustrating an example technique for providing operational power to implantable trial IMD 32. Although trial IMD 32 is described in FIG. 7, any other trial IMD (e.g., trial IMD 14) may receive the operational power instead. As shown in FIG. 7, powering device 20 may receive user input (150). The user input may be a request to transmit power to trial IMD 32, adjust one or more parameters of powering device 20, or otherwise manage the trial stimulation therapy. If the user input does not request stimulation to be delivered ("NO" branch of block 152), powering device 20 may again wait to receive user input.

If the user input requests that stimulation is to be provided to patient 12 ("YES" branch of block 152), then power module 138 may generate the electrical signal used by powering device 20 to transmit power to trial IMD 32 (154). Power module 138 may then drive the electrical signal through primary coil 140 to generate a magnetic field configured to transmit power to secondary coil 92 of trial IMD 32. Power module 138 may continue to drive the electrical signal through coil 92 until powering device 20 receives a request to discontinue power transmission or power transmission is stopped by a timer or other automatically generated signal.

Figure 8:
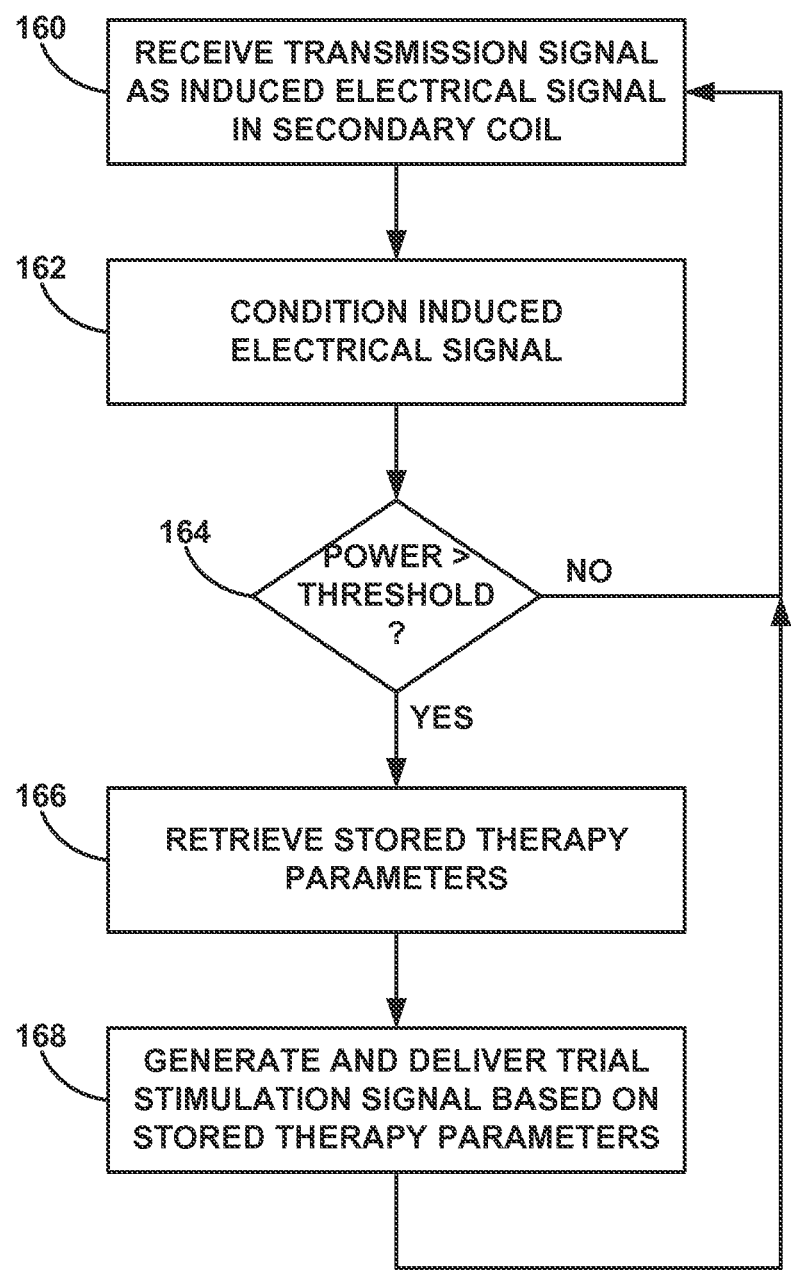
FIG. 8 is a flow diagram illustrating an example technique for delivering trial stimulation from an external powering device.

FIG. 8 is a flow diagram illustrating an example technique for delivering trial stimulation with trial IMD 32 using power from an external powering device 20. Although trial IMD 32 is described in FIG. 8, any other trial IMD (e.g., trial IMD 14) may receive the operational power instead. The technique of FIG. 8 may be associated with the technique of FIG. 7. As shown in FIG. 8, secondary coil 92 of trial IMD 32 may receive a transmission signal from primary coil 140 of powering device 20 (160). The transmission signal may be from a magnetic field generated by primary coil 140. In addition, the transmission signal may induce an electrical signal in secondary coil 92. The induced electrical signal may be used to provide operational power to the circuitry of trial IMD 32.

Power module 98 of trial IMD 32 may then condition the induced electrical signal into a signal usable by the circuitry of trial IMD 32 (162). Conditioning the induced electrical signal may include rectifying, filtering, converting, regulating, or any other transformation of the electrical signal such that operational power is produced. Power module 98 may rectify the alternating current of the induced electrical signal to a direct current signal. Power module 98 may also filter the induced electrical signal as needed to a frequency usably by the circuitry of trial IMD 32 (e.g., therapy module 102).

If the power output by power module 98 is below an operational threshold level ("NO" branch of block 164), trial IMD 32 may continue to receive the transmission signal (160). The operational threshold may be based on a voltage level, a current level, or both.

If the power output by power module 98 is above the operation threshold level ("YES" branch of block 164), then therapy module 102 may retrieve stored trial therapy parameters from memory 104 (166). The trial therapy parameters may define the trial stimulation therapy to be delivered to patient 12. Therapy module 102 may then generate the trial stimulation signal based on the trial therapy parameters and deliver the trial stimulation signal to patient 12 via lead 34 and electrodes 36 (168). The trial stimulation signal may be a series of electrical pulses or a continuous waveform selected to alleviate the condition of patient 12. Trial IMD 32 may then continue to receive power from the transmission signal (160) in order to continue delivering trial stimulation therapy to patient 12.

Figure 9:
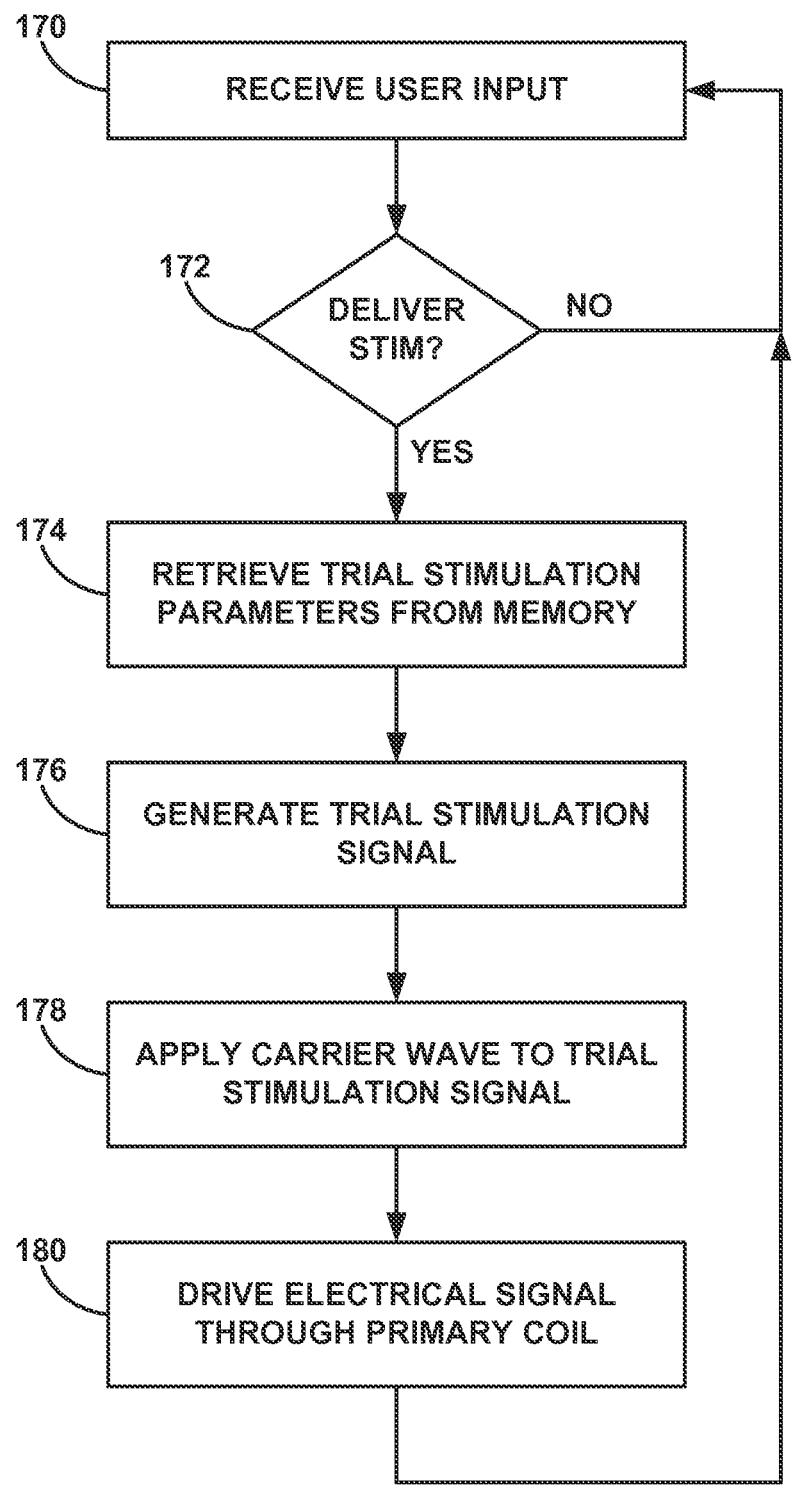
FIG. 9 is a flow diagram illustrating an example technique for providing trial stimulation signal to an implantable trial neurostimulator using inductive coupling.

FIG. 9 is a flow diagram illustrating an example technique for providing a trial stimulation signal to trial IMD 114 using inductive coupling. Although trial IMD 114 is described in FIG. 9, any other trial IMD (e.g., trial IMD 14) may receive the stimulation signal directly from powering device 20. As shown in FIG. 9, powering device 20 may receive user input (170). The user input may be a request to transmit power to trial IMD 114, adjust one or more stimulation parameters of powering device 20, select one or more trial stimulation parameters, select a trial stimulation program, or otherwise manage the trial stimulation therapy. If the user input does not request stimulation to be delivered ("NO" branch of block 172), powering device 20 may again wait to receive user input.

If the user input requests that stimulation is to be provided to patient 12 ("YES" branch of block 172), then power module 138 may retrieve trial stimulation parameters from memory 132 that define the stimulation signal for treating patient 12 (174). Power module 138 may then generate the trial stimulation signal based on the trial stimulation parameters (176). The trial stimulation signal alone may not be sufficient for transmission wirelessly through the skin of patient 12 and to trial IMD 114. Therefore, power module 138 may apply a carrier wave to the trial stimulation signal such that a sufficient electrical signal is generated for transmission (178). The carrier wave may be a high-frequency carrier wave having sufficient energy to create the magnetic field needed to induce an electrical signal within trial IMD 114.

Power module 138 may then drive the electrical signal (e.g., the carrier wave and stimulation signal) through primary coil 140 to generate a magnetic field configured to transmit the trial stimulation signal to secondary coil 116 of trial IMD 114. In other words, the lower frequency stimulation signal may modulate the higher frequency carrier signal. The resulting electrical signal may include a high frequency that is modulated, or one or more properties changes over time, to include the parameters of the stimulation signal. A low-pass filter, and additional filters in some examples, in the trial IMD 114 may filter out the higher frequency carrier signal. The transmitted stimulation signal may thus include sufficient power to deliver stimulation to patient 12. Power module 138 may continue to drive the electrical signal through coil 116 until powering device 20 receives a request to discontinue signal transmission or signal transmission is stopped by a timer or other automatically generated signal.

In other examples, power module 138 may not generate the stimulation signal. Instead, a therapy module within powering device 20 may generate the stimulation signal and transmit the stimulation signal to power module 138 for transmission to trial IMD 114. In this manner, separate modules, or circuits, may perform the tasks of generating the stimulation signal and generating the electrical signal for wireless transmission. In any case, powering device 20 may generate the stimulation signal such that a therapy module is not needed within trial IMD 114.

Figure 10:
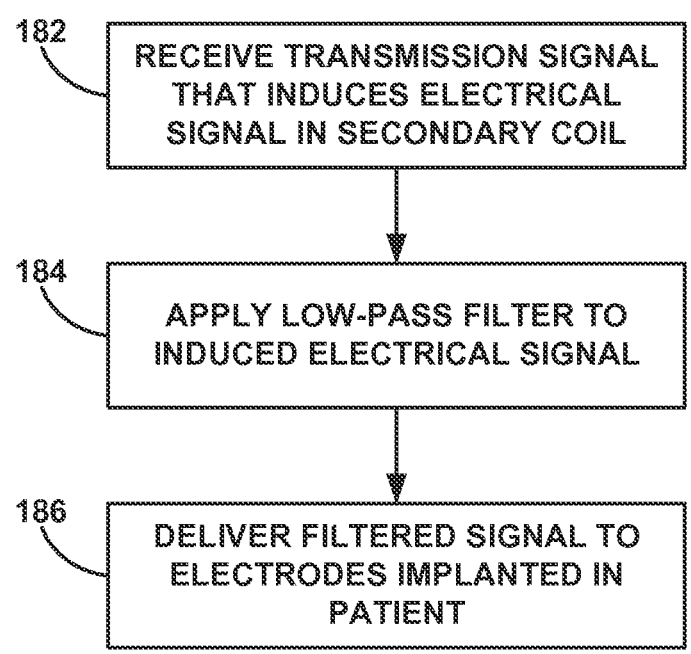
FIG. 10 is a flow diagram illustrating an example technique for delivering trial stimulation from a transmission signal received from an external device using inductive coupling.

FIG. 10 is a flow diagram illustrating an example technique for delivering trial stimulation from a transmission signal received from an external powering device 20 using inductive coupling. The technique of FIG. 10 may be associated with the technique of FIG. 9. Although trial IMD 114 is described in FIG. 9, any other trial IMD (e.g., trial IMD 14) may receive the stimulation signal directly from powering device 20. As shown in FIG. 10, secondary coil 116 of trial IMD 114 may receive a transmission signal from primary coil 140 of powering device 20 (182). The transmission signal may be from a magnetic field generated by primary coil 140. In addition, the transmission signal may induce an electrical signal in secondary coil 116.

The induced electrical signal may include the stimulation signal over a high-frequency carrier signal. Therefore, filter module 118 may apply a low-pass filter to the induced electrical signal to extract the stimulation signal from the high-frequency carrier signal (184). In some examples, filter module 118 may apply two or more different filters that condition the induced electrical signal into a signal appropriate for delivery to patient 12. Trial IMD 114 may then deliver the filtered signal to electrodes 120A and 120B of a lead coupled to Trial IMD 114. In this manner, trial stimulation therapy is only delivered to patient 12 in response to receiving the transmission signal from powering device 20.

In other examples, trial IMD 114 may provide additional processing, conditioning, rectifying, or amplification of the induced electrical signal. For example, one or more circuits within trial IMD 114 may rectify an alternating current of the induced electrical signal to a direct current. In another example, trial IMD 114 may amplify the filtered signal after filter module 118. In any case, the stimulation signal delivered by trial IMD 114 may be configured to emulate chronic stimulation therapy without needing to implant a fully functional neurostimulator.

According to the techniques and devices described herein, a trial implantable neurostimulator may be provided that includes minimal circuitry to minimize size and cost of the trial neurostimulator. The trial neurostimulator may receive power, or even the stimulation signal, directly from an external powering device instead of including a battery power within the neurostimulator. The trial neurostimulator may also include a housing that is non-hermetic. This non-hermetic housing may protect the circuitry of the trial neurostimulator for the trial period, but the non-hermetic housing may non-functional for chronic therapy. In addition, the trial neurostimulator may be permanently or removably coupled to an implantable lead. A removably coupled trial neurostimulator may allow the lead to be a chronic lead that is coupled to a chronic neurostimulator instead of being replaced after successful trial therapy.

Various examples have been described. These and other examples are within the scope of the following claims.

The invention claimed is:

1. An implantable medical device comprising:
   a secondary coil configured to generate an electrical signal in response to a magnetic field generated by an external primary coil;
   circuitry configured to generate, in response to the electrical signal, an electrical stimulation signal deliverable to a patient; and
   a non-hermetic implantable housing configured to house the circuitry.

2. The implantable medical device of claim 1, wherein the non-hermetic implantable housing is further configured to house the secondary coil.

3. The implantable medical device of claim 1, further comprising an implantable medical lead configured to be removably coupled to the circuitry, wherein the medical lead is configured to electrically couple with a chronic implantable medical device.

4. The implantable medical device of claim 1, further comprising:
   an implantable medical lead configured to deliver the electrical stimulation signal to the patient; and
   an implantable lead extension permanently coupled to the circuitry and at least partially covered by the housing, wherein the implantable lead extension is configured to electrical couple the circuitry to the medical lead.

5. The implantable medical device of claim 1, further comprising an implantable medical lead permanently coupled to the circuitry and at least partially covered by the housing, wherein the medical lead delivers the electrical stimulation signal to the patient.

6. The implantable medical device of claim 1, wherein the non-hermetic implantable housing is formed by an epoxy, the epoxy being a non-hermetic material.

7. The implantable medical device of claim 1, wherein the non-hermetic implantable housing is constructed of at least one material that comprises a helium permeability greater than approximately $1\times10^{-8}$ cubic centimeters per second at zero degrees Celsius and one atmosphere pressure.

8. The implantable medical device of claim 1, wherein the non-hermetic implantable housing is constructed of at least one material that comprises a helium permeability greater than approximately $1\times10^{-3}$ cubic centimeters per second at zero degrees Celsius and one atmosphere pressure.

9. The implantable medical device of claim 1, wherein the non-hermetic implantable housing comprises a volume less than approximately 7.0 cubic centimeters.

10. The implantable medical device of claim 1, wherein the circuitry comprises:
    a power module configured to rectify the electrical signal from an alternating current to a direct current;
    a memory configured to store at least one set of trial stimulation therapy parameters that define the electrical stimulation signal; and
    a therapy module configured to generate the electrical stimulation signal, and wherein the rectified electrical signal is configured to power the therapy module.

11. The implantable medical device of claim 1, wherein the circuitry comprises a filter module configured to output the electrical stimulation signal when the electrical signal is applied directly to the filter module.

12. A system comprising:
    means for generating an electrical signal in response to a magnetic field generated by an external primary coil;
    means for generating, in response to the electrical signal, an electrical stimulation signal deliverable to a patient;
    means for delivering the stimulation signal to the patient; and
    means for non-hermetically housing the means for generating the electrical signal and the means for generating the electrical stimulation signal within the patient.

13. The system of claim 12, wherein the means for delivering the electrical stimulation signal comprises means for removably coupling the means for delivering the electrical stimulation signal to the means for generating the stimulation signal.

14. The system of claim 12, wherein the means for delivering the electrical stimulation signal is permanently coupled to the means for generating the electrical stimulation signal and at least partially covered by the non-hermetic housing means.

15. The system of claim 12, wherein the non-hermetic housing means is formed by an epoxy, the epoxy being a non-hermetic material.

16. The system of claim 12, wherein the non-hermetic housing means comprises a helium permeability greater than approximately $1\times10^{-8}$ cubic centimeters per second at zero degrees Celsius and one atmosphere pressure.

17. The system of claim 12, wherein the non-hermetic housing means comprises a helium permeability greater than approximately $1\times10^{-3}$ cubic centimeters per second at zero degrees Celsius and one atmosphere pressure.

18. The system of claim 12, wherein the non-hermetic housing means comprises a volume less than approximately 7.0 cubic centimeters.

19. The system of claim 12, further comprising:
    means for rectifying the electrical signal from an alternating current to a direct current, wherein the rectified electrical signal is configured to power the means for generating the electrical stimulation signal; and
    means for storing at least one set of trial stimulation therapy parameters that define the electrical stimulation signal.

20. The system of claim 12, wherein the means for generating the electrical stimulation signal comprises means for filtering the electrical signal, wherein the filtered electrical signal is the electrical stimulation signal.

21. The system of claim 12, further comprising means for generating the magnetic field external to the patient, wherein electrical parameters that define the magnetic field are selected to transmit operating power to the means for generating the electrical stimulation signal.

22. The system of claim 12, further comprising means for generating the magnetic field external to the patient, wherein electrical parameters that define the magnetic field are selected to induce the electrical signal containing the electrical simulation signal.

23. A method comprising:
    generating an electrical signal by a secondary coil in response to a magnetic field generated by an external primary coil; and
    generating, in response to the electrical signal and by circuitry, an electrical stimulation signal deliverable to a patient, wherein the secondary coil and the circuitry are housed by a non-hermetic housing implanted within the patient.

24. The method of claim 23, further comprising delivering the electrical stimulation signal to the patient by a medical lead coupled to the circuitry.

25. The method of claim 24, wherein the secondary coil and the circuitry are housed by the non-hermetic housing of a trial implantable medical device, further comprising:

removing the trial implantable medical device from the medial lead and the patient after a trial period; and coupling the medical lead to a chronic implantable medical device after successful trial stimulation generated by the trial implantable medical device.

26. The method of claim 25, wherein the trial period is less than approximately four weeks.

27. The method of claim 23, wherein the non-hermetic housing comprises an epoxy and a volume less than approximately 7.0 cubic centimeters.

28. The method of claim 23, further comprising receiving power from an external powering device by the secondary coil within the patient.

29. The method of claim 23, further comprising generating the magnetic field with a primary coil of an external power device.

30. A system comprising:
an implantable medical device comprising:
  a secondary coil configured to generate an electrical signal in response to a magnetic field generated by an external primary coil;
  circuitry configured to generate, in response to the electrical signal, an electrical stimulation signal deliverable to a patient;
  a non-hermetic housing configured to house the secondary coil and the circuitry; and
  a medical lead permanently coupled to the circuitry and at least partially covered by the non-hermetic housing, wherein the medical lead is configured to deliver the electrical stimulation signal to the patient; and
an introducer comprising:
  a sheath configured to accept at least a portion of the medical lead, wherein the sheath comprises at least one structural characteristic configured to facilitate splitting the sheath along a length of the sheath; and
  a handle configured to separate the sheath along the at least one structural characteristic in response to a force directed away from the implantable medical device.

* * * * *